United States Patent
Steinke et al.

(10) Patent No.: US 6,623,521 B2
(45) Date of Patent: *Sep. 23, 2003

(54) EXPANDABLE STENT WITH SLIDING AND LOCKING RADIAL ELEMENTS

(75) Inventors: Thomas A. Steinke, San Diego, CA (US); Donald H. Koenig, San Diego, CA (US); Joan Zeltinger, Encinitas, CA (US)

(73) Assignee: MD3, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/739,552

(22) Filed: Dec. 14, 2000

(65) Prior Publication Data

US 2001/0044651 A1 Nov. 22, 2001

Related U.S. Application Data

(63) Continuation-in-part of application No. 09/283,800, filed on Apr. 1, 1999, now Pat. No. 6,224,626, which is a continuation-in-part of application No. 09/024,571, filed on Feb. 17, 1998, now Pat. No. 6,033,436.

(51) Int. Cl.[7] .................................................. A61F 2/06
(52) U.S. Cl. ...................................... 623/1.16; 623/1.15
(58) Field of Search ............................ 623/1.16, 1.15, 623/1.27, 1.3, 1.42

(56) References Cited

U.S. PATENT DOCUMENTS

| | | | |
|---|---|---|---|
| 3,620,218 A | 11/1971 | Schmitt | |
| 4,553,545 A | 11/1985 | Maass et al. | |
| 4,733,665 A | 3/1988 | Palmaz | |
| 4,739,762 A | 4/1988 | Palmaz | |
| 4,776,337 A | 10/1988 | Palmaz | |

(List continued on next page.)

FOREIGN PATENT DOCUMENTS

| | | |
|---|---|---|
| WO | WO 96/14030 | 5/1996 |
| WO | WO 98/22045 | 5/1998 |
| WO | WO 99/40874 | 8/1999 |

OTHER PUBLICATIONS

Yanhua Hu, MD, *Inhibition of Neointima Hyperplasia of Mouse Vein Grafts by Locally Applied Suramin,* Circulation, vol. 100, Aug. 24, 1999, pp. 861–868.

Hideo Yasukawa, MD, *Inhibition of Intimal Hyperplasia After Balloon Injury by Antibodies to Intercellular Adhesion Molecule–1 and Lymphocyte Function? Associated Antigen–1,* Circulation, vol. 95, 1997 pp. 1515–1522.

Carmeliel, MD, et al, *Inhibitory Role of Plasminogen Activator Inhibitor–1 in Arterial Wound Healing and Neointima Formation,* Circulation, vol. 96, 1997, pp. 3180–3191.

Robert M. Nerem, et al., *Tissue Engineering and The Vascular System, Synthetic Biodegradable Polymer Scaffolds,* (1997) pp. 164–185.

Ron Brauner, MD, *Controlled Periadventitial Administration of Verapamil Inhibits Neointimal Smooth Muscle Cell Proliferation and Ameliorates Vasomotor Abnormalities in Experimental Vein Bypass Grafts,* The Journal of Thoracic and Cardiovascular Surgery, Jul. 1997, vol. 114, No. 1, pp. 53–63.

(List continued on next page.)

Primary Examiner—Bruce Snow
(74) Attorney, Agent, or Firm—Knobbe, Martens, Olson & Bear, LLP

(57) ABSTRACT

The present invention provides a lumen support stent with a clear through-lumen for use in a body lumen. The stent is formed from at least one series of sliding and locking radial elements and at least one ratcheting mechanism comprising an articulating element and a plurality of stops. The ratcheting mechanism permits one-way sliding of the radial elements from a collapsed diameter to an expanded diameter, but inhibits radial recoil from the expanded diameter.

29 Claims, 17 Drawing Sheets

U.S. PATENT DOCUMENTS

| | | |
|---|---|---|
| 4,922,905 A | 5/1990 | Strecker |
| 5,059,211 A | 10/1991 | Stack et al. |
| 5,192,307 A | 3/1993 | Wall |
| 5,195,984 A | 3/1993 | Schatz |
| 5,266,073 A | 11/1993 | Wall |
| 5,306,286 A | 4/1994 | Stack et al. |
| 5,306,294 A | 4/1994 | Winston et al. |
| 5,397,355 A | 3/1995 | Marin et al. |
| 5,423,885 A | 6/1995 | Williams |
| 5,441,515 A | 8/1995 | Khosravi et al. |
| 5,443,500 A | 8/1995 | Sigwart |
| 5,449,382 A | 9/1995 | Dayton |
| 5,464,450 A | 11/1995 | Buscemi et al. |
| 5,476,508 A | 12/1995 | Amstrup |
| 5,527,337 A | 6/1996 | Stack et al. |
| 5,549,662 A | 8/1996 | Fordenbacher |
| 5,551,954 A | 9/1996 | Buscemi et al. |
| 5,556,413 A | 9/1996 | Lam |
| 5,578,075 A | 11/1996 | Dayton |
| 5,591,223 A | 1/1997 | Lock et al. |
| 5,603,722 A | 2/1997 | Phan et al. |
| 5,618,299 A | 4/1997 | Khosravi et al. |
| 5,629,077 A | 5/1997 | Turnlund et al. |
| 5,632,771 A | 5/1997 | Boatman et al. |
| 5,643,312 A | 7/1997 | Fischell et al. |
| 5,643,314 A | 7/1997 | Carpenter et al. |
| 5,643,339 A | 7/1997 | Kavteladze et al. |
| 5,649,977 A | 7/1997 | Campbell |
| 5,707,387 A | 1/1998 | Wijay |
| 5,725,549 A | 3/1998 | Lam |
| 5,733,328 A | 3/1998 | Fordenbacher |
| 5,735,872 A | 4/1998 | Carpenter et al. |
| 5,741,293 A | 4/1998 | Wijay |
| 5,766,710 A | 6/1998 | Turnlund et al. |
| 5,851,217 A | 12/1998 | Wolff et al. |
| 5,851,231 A | 12/1998 | Wolff et al. |
| 5,876,419 A | 3/1999 | Carpenter et al. |

OTHER PUBLICATIONS

Yoshihiro Kurisu, et al., *Protective Effect of Beraprost Sodium, a Stable Prostacyclin Analogue, on Cardiac Allograft Vasculopathy in Rats,* Hiroshima J. Med. Sci. vol. 46, No. 1, Mar. 1997, pp. 11–19.

S. Nikol, et al., *Molecular biology and post–angioplasty restenosis,* Atherosclerosis 123 (1996) pp. 17–31.

Takayuki Asahara, MD, *Local Delivery of Vascular Endothelial Growth Factor Accelerates Reendothelialization and Attenuates Intimal Hyperplasia in Balloon–Insured Rate Carotid Artery,* Circulation, vol. 91, (1995) pp. 2793–2801.

Takayuki Asahara, MD, et al., *Synergistic Effect of Vascular Endothelial Growth Factor and Basic Fibroblast Growth Factor on Angiogenesis In Vivo,* Supplement II Circulation, vol. 92, No. 9, Nov. 1, 1995, pp. II–365–371.

Heiko E. Von Der Leyen, et al., *Gene therapy neointimal vascular lesion: In vivo transfer of endothelial cell nitric oxide synthase gene,* Proc. Natl. Acad. Sci. USA, vol. 92, Feb. 1995, pp. 1137–1141.

Michael V. Autieri, et al., *Antisense Oligonucleotides to the P65 Subunit of NF–Kb Inhibit Human Vascular Smooth Muscle Cell Adherence and Proliferation and Prevent Neointima Formation in Rat Carotid Arteries,* Biochemical and Biophysical Research Communications, vol. 213, No. 3, (1995) pp. 827–836.

Jean Francois Tanguay, MD, et al. *Current Status of Biodegradable Stents, Contemporary Interventional Techniques,* vol. 12 No. 4, Nov. 1994, pp. 699–713.

Ryuichi Morishita et al., *Novel In Vitro Gene Transfer Method for Study of Local Modulators in Vascular Smooth Muscle Cells,* Hypertension, vol. 21, No. 6, Part 2 Jun. 1993, pp. 894–899.

Stephen E. Epstein, MD, et al., *Cytotoxic Effects of a Recombinant Chimeric Toxin on Rapidly Proliferating Vascular Smooth Muscle Cells,* Circulation, vol. 84, No. 2, Aug. 1991, pp. 778–787.

EXPANDABLE STENT WITH SLIDING AND LOCKING RADIAL ELEMENTS

RELATED APPLICATIONS

This is a continuation-in-part application and claims priority under 35 U.S.C. §120 to U.S. patent application Ser. No. 09/283,800 filed on Apr. 1, 1999, now U.S Pat. No. 6,224,626, which is a continuation-in-part of U.S. patent application Ser. No. 09/024,571 filed on Feb. 17, 1998, now U.S. Pat. No. 6,033,436.

BACKGROUND OF THE INVENTION

This invention relates to expandable medical implants for maintaining support of a body lumen.

An important use of stents is found in situations where part of the vessel wall or stenotic plaque blocks or occludes fluid flow in the vessel. Often, a balloon catheter is utilized in a percutaneous transluminal coronary angioplasty procedure to enlarge the occluded portion of the vessel. However, the dilation of the occlusion can cause fissuring of atherosclerotic plaque and damage to the endothelium and underlying smooth muscle cell layer, potentially leading to immediate problems from flap formation or perforations in the vessel wall, as well as long-term problems with restenosis of the dilated vessel. Implantation of stents can provide support for such problems and prevent re-closure of the vessel or provide patch repair for a perforated vessel. Further, the stent may overcome the tendency of diseased vessel walls to collapse, thereby maintaining a more normal flow of blood through that vessel.

Significant difficulties have been encountered with all prior art stents. Each has its percentage of thrombosis, restenosis and tissue in-growth, as well as various design-specific disadvantages.

Examples of prior developed stents have been described by Balcon et al., "Recommendations on Stent Manufacture, Implantation and Utilization," European Heart Journal (1997), vol. 18, pages 1536–1547, and Phillips, et al., "The Stenter's Notebook," Physician's Press (1998), Birmingham, Mich. The first stent used clinically was the self-expanding "Wallstent" which comprised a metallic mesh in the form of a Chinese fingercuff. This design concept serves as the basis for many stents used today. These stents were cut from elongated tubes of wire braid and, accordingly, had the disadvantage that metal prongs from the cutting process remained at the longitudinal ends thereof. A second disadvantage is the inherent rigidity of the cobalt based alloy with a platinum core used to form the stent, which together with the terminal prongs, makes navigation of the blood vessels to the locus of the lesion difficult as well as risky from the standpoint of injury to healthy tissue along the passage to the target vessel. Another disadvantage is that the continuous stresses from blood flow and cardiac muscle activity create significant risks of thrombosis and damage to the vessel walls adjacent to the lesion, leading to restenosis. A major disadvantage of these types of stents is that their radial expansion is associated with significant shortening in their length, resulting in unpredictable longitudinal coverage when fully deployed.

Among subsequent designs, some of the most popular have been the Palmaz-Schatz slotted tube stents. Originally, the Palmaz-Schatz stents consisted of slotted stainless steel tubes comprising separate segments connected with articulations. Later designs incorporated spiral articulation for improved flexibility. These stents are delivered to the affected area by means of a balloon catheter, and are then expanded to the proper size. The disadvantage of the Palmaz-Schatz designs and similar variations is that they exhibit moderate longitudinal shortening upon expansion, with some decrease in diameter, or recoil, after deployment. Furthermore, the expanded metal mesh is associated with relatively jagged terminal prongs, which increase the risk of thrombosis and/or restenosis. This design is considered current state of the art, even though their thickness is 0.004 to 0.006 inches.

Another type of stent involves a tube formed of a single strand of tantalum wire, wound in a sinusoidal helix; these are known as coil stents. They exhibit increased flexibility compared to the Palnaz-Schatz stents. However, they have the disadvantage of not providing sufficient scaffolding support for many applications, including calcified or bulky vascular lesions. Further, the coil stents also exhibit recoil after radial expansion.

One stent design described by Fordenbacher, employs a plurality of elongated parallel stent components, each having a longitudinal backbone with a plurality of opposing circumferential elements or fingers. The circumferential elements from one stent component weave into paired slots in the longitudinal backbone of an adjacent stent component. By incorporating locking means within the slotted articulation, the Fordenbacher stent may minimize recoil after radial expansion. In addition, sufficient numbers of circumferential elements in the Fordenbacher stent may provide adequate scaffolding. Unfortunately, the free ends of the circumferential elements, protruding through the paired slots, may pose significant risks of thrombosis and/or restenosis. Moreover, this stent design would tend to be rather inflexible as a result of the plurality of longitudinal backbones.

Some stents employ "jelly roll" designs, wherein a sheet is rolled upon itself with a high degree of overlap in the collapsed state and a decreasing overlap as the stent unrolls to an expanded state. Examples of such designs are described in U.S. Pat. No. 5,421,955 to Lau, U.S. Pat. Nos. 5,441,515 and 5,618,299 to Khosravi, and U.S. Pat. No. 5,443,500 to Sigwart. The disadvantage of these designs is that they tend to exhibit very poor longitudinal flexibility. In a modified design that exhibits improved longitudinal flexibility, multiple short rolls are coupled longitudinally. See e.g., U.S. Pat. No. 5,649,977 to Campbell and U.S. Pat. Nos. 5,643,314 and 5,735,872 to Carpenter. However, these coupled rolls lack vessel support between adjacent rolls.

Another form of metal stent is a heat expandable device using Nitinol or a tin-coated, heat expandable coil. This type of stent is delivered to the affected area on a catheter capable of receiving heated fluids. Once properly situated, heated saline is passed through the portion of the catheter on which the stent is located, causing the stent to expand. The disadvantages associated with this stent design are numerous. Difficulties that have been encountered with this device include difficulty in obtaining reliable expansion, and difficulties in maintaining the stent in its expanded state.

Self-expanding stents are also available. These are delivered while restrained within a sleeve (or other restraining mechanism), that when removed allows the stent to expand. Self-expanding stents are problematic in that exact sizing, within 0.1 to 0.2 mm expanded diameter, is necessary to adequately reduce restenosis. However, self-expanding stents are currently available only in 0.5 mm increments. Thus, greater selection and adaptability in expanded size is needed.

In summary, there remains a need for an improved stent: one that has smoother marginal edges, to minimize restenosis; one that is small enough and flexible enough when collapsed to permit uncomplicated delivery to the affected area; one that is sufficiently flexible upon deployment to conform to the shape of the affected body lumen; one that expands uniformly to a desired diameter, without change in length; one that maintains the expanded size, without significant recoil; one that has sufficient scaffolding to provide a clear through-lumen; one that employs a thinner-walled design, which can be made smaller and more flexible to reach smaller diameter vessels; and one that has a thinner-walled design to permit faster endothelialization or covering of the stent with vessel lining, which in turn minimizes the risk of thrombosis from exposed stent materials.

SUMMARY OF THE INVENTION

The present invention relates to an expandable intraluminal stent, comprising a tubular member with a clear through-lumen. The tubular member has proximal and distal ends and a longitudinal length defined therebetween, and a circumference, and a diameter which is adjustable between at least a first collapsed diameter and at least a second expanded diameter. In a preferred mode, the longitudinal length remains substantially unchanged when the tubular member is adjusted between the first collapsed diameter and the second expanded diameter. The tubular member includes at least one module comprising a series of sliding and locking radial elements, wherein each radial element defines a portion of the circumference of the tubular member and where no radial element overlaps with itself in either the first collapsed diameter or the second expanded diameter.

In one aspect, each radial element may comprise at least one elongated rib disposed between first and second end portions. Preferably, the radial elements that comprise a module alternate between radial elements having an odd number of elongated ribs and radial elements having an even number of elongated ribs. In one preferred mode, the radial elements alternate between radial elements having one elongated rib and radial elements having two elongated ribs.

The stent also includes at least one articulating mechanism comprising a tab and at least one stop. The articulating mechanism permits one-way sliding of the radial elements from the first collapsed diameter to the second expanded diameter, but inhibits radial recoil from the second expanded diameter.

In variations to the stent, the tubular member may comprise at least two modules which are coupled to one another by at least one linkage element. In one variation, the tubular member may further comprise a frame element that surrounds at least one radial element in each module. In stents in which the tubular member comprises at least two modules, such frame elements from adjacent modules may be coupled. The coupling may include a linkage element extending between the frame elements. In addition or in the alternative, the frame elements from adjacent modules may be coupled by interlinking of the frame elements. In another aspect, the intermodular coupling may be degradable allowing for the independent modules to adapt to the vessel curvature.

In another variation to the stent of the present invention, any amount of overlap among the radial elements within in a module remains constant as the tubular member is adjusted from the first collapsed diameter to the second expanded diameter. This amount of overlap is preferably less than about 15%.

The radial recoil of the tubular member in accordance with one preferred embodiment is less than about 5%. The stiffness of the stent is preferably less than about 0.1 Newtons force/millimeter deflection. The tubular member also preferably provides a surface area coverage of greater than about 20%.

In accordance with another variation of the present stent, the tubular member is at least partially radiopaque. The radial elements may be made substantially from a material which is work hardened to between about 80% and 95%. In one preferred variation, the radial elements in the expandable intraluminal stent are made from a material selected from the group consisting of a polymer, a metal, a ceramic, and combinations thereof. In one mode, the material may be degradable.

In another mode of the invention, the material may also include a bioactive agent. The material is preferable adapted to deliver an amount of the bioactive agent which is sufficient to inhibit restenosis at the site of stent deployment. In one variation, the radial elements are adapted to release the bioactive agent during stent deployment when the tubular member is adjusted from the first collapsed diameter to the second expanded diameter. The bioactive agent(s) is preferably selected from the group consisting of antiplatelet agents, antithrombin agents, antiproliferative agents, and antiinflammatory agents.

In another variation, the tubular member further comprises a sheath, such as for example in a vessel graft.

In one aspect, the expandable intraluminal stent comprises at least two modules, wherein the expanded diameters of the first and second modules are different.

The articulating mechanism(s) of the present invention which allow the stent to expand but inhibit stent recoil, may comprise a slot and a tab on one radial element and at least one stop on an adjacent radial element which is slideably engaged in the slot, wherein the tab is adapted to engage the at least one stop. The articulating mechanism(s) may also include an expansion resistor on the slideably engaged radial element, wherein the expansion resistor resists passing through the slot during expansion until further force is applied, such that the radial elements in the module expand in a substantially uniform manner. In another variation, the articulating mechanism may include a release, such that actuation of the release permits sliding of the radial elements from the second expanded diameter back to the first collapsed diameter for possible removal of the stent. In another variation, the stent may comprise a floating coupling element having an articulating mechanism.

In another variation, the expandable intraluminal stent comprises a tubular member with a clear through-lumen and a diameter which is adjustable between at least a first collapsed diameter and at least a second expanded diameter. The tubular member comprises a series of sliding and locking radial elements made from a degradable material, wherein each radial element in the series defines a portion of the circumference of the tubular member and wherein no radial element overlaps itself. This stent also has at least one articulating mechanism that permits one-way sliding of the radial elements from the first collapsed diameter to the second expanded diameter, but inhibits radial recoil from the second expanded diameter. The degradable material may be selected from the group consisting of polyarylates (L-tyrosine-derived), free acid polyarylates, polycarbonates (L-tyrosine-derived), poly(ester-amides), poly(propylene fumarate-co-ethylene glycol) copolymer, polyanhydride esters, polyanhydrides, polyorthoesters, and silk-elastin polymers, calcium phosphate, magnesium alloys or blends thereof.

In a variation to the degradable stent, the degradable polymer may further comprise at least one bioactive agent, which is released as the material degrades. The at least one bioactive agent may be selected from the group consisting of antiplatelet agents, antithrombin agents, antiproliferative agents and antiinflammatory agents.

In another variation, the stent material may be fiber-reinforced. The reinforcing material may be a degradable material such as calcium phosphate (e.g., BIOGLASS). Alternatively, the fibers may be fiberglass, graphite, or other non-degradable material.

In another mode, the stent of the present invention comprises a tubular member having a wall and a clear through-lumen. The tubular member comprises a series of sliding and locking radial elements which do not overlap with themselves. The radial elements further comprise a ratcheting mechanism that permits own-way sliding of the radial elements from a first collapsed diameter to a second expanded diameter. The tubular member in this embodiment has a stiffness of less than about 0.1 Newtons force/millimeter deflection, and the wall of the tubular member has a thickness of less than about 0.005 inches.

DETAILED DESCRIPTION OF THE PREFERRED EMBODIMENT

Stent Design

Figures 1A, 1B, 1C:
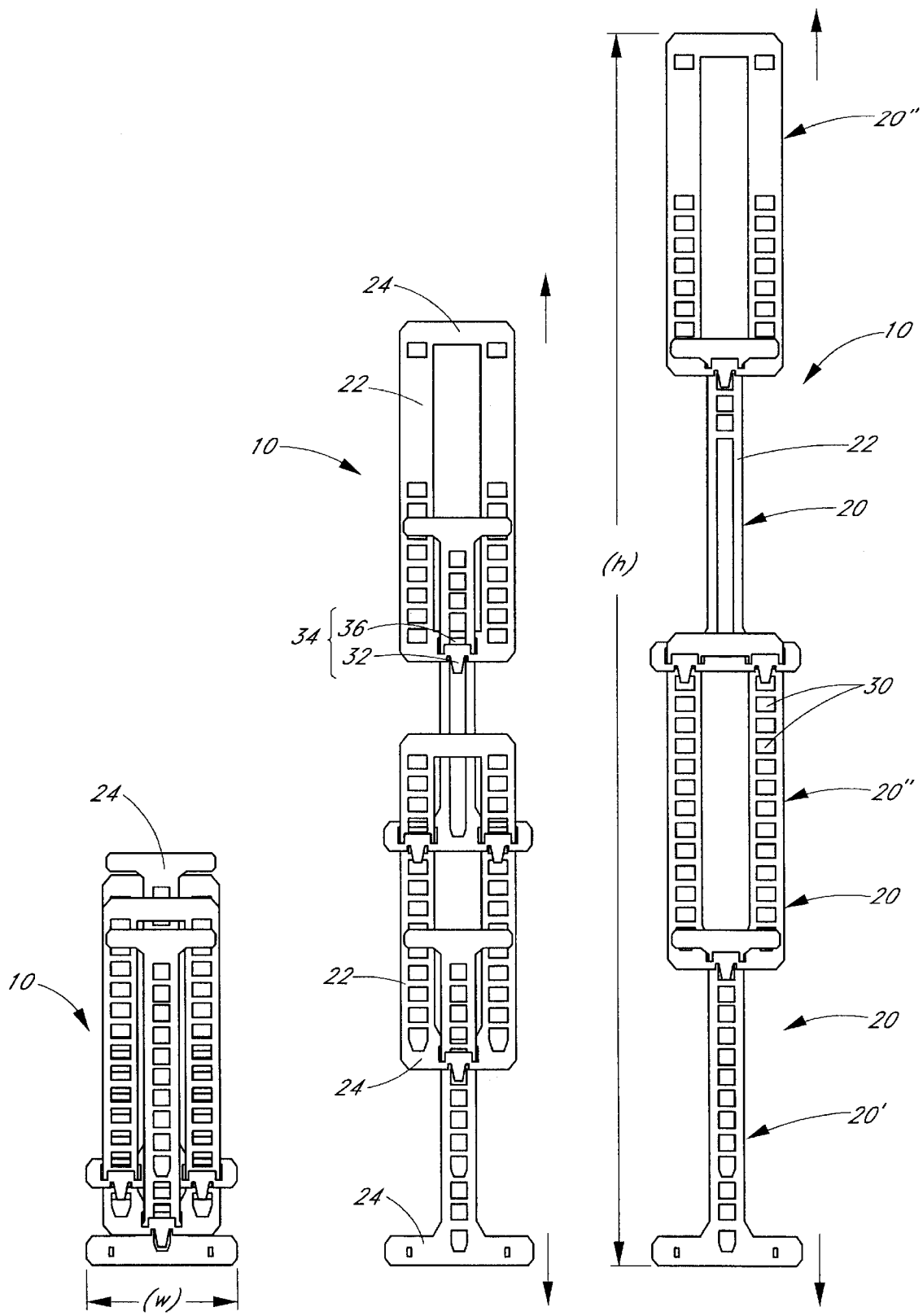
FIGS. 1A–C are plan views of one module of an expandable stent in accordance with the present invention, illustrating a series of radial elements. The assembled module is shown in various states, from a collapsed state (FIG. 1A), to a partially expanded state (FIG. 1B), to an expanded state (FIG. 1C).

The present invention relates to a radially expandable stent used to open, or to expand a targeted area in a body lumen. In one preferred embodiment of the present invention, the assembled stent comprises a tubular member having a length in the longitudinal axis and a diameter in the radial axis, of appropriate size to be inserted into the body lumen. The length and diameter of the tubular member may vary considerably for deployment in different selected target lumens depending on the number and configuration of the structural components, described below. The tubular member is adjustable from at least a first collapsed diameter to at least a second expanded diameter. One or more stops and engaging elements or tabs are incorporated into the structural components of the tubular member whereby recoil (i.e., collapse from an expanded diameter to a more collapsed diameter) is minimized to less than about 5%.

The tubular member in accordance with the present invention has a "clear through-lumen," which is defined as having no structural elements protruding into the lumen in either the collapsed or expanded diameters. Further, the tubular member has smooth marginal edges to minimize the trauma of edge effects. The tubular member is preferably thin-walled (wall thickness depending on the selected materials ranging from less than about 0.006 inches for plastic and degradable materials to less than about 0.002 inches for metal materials) and flexible to facilitate delivery to small vessels and through tortuous vasculature. The thin walled design will also minimize blood turbulence and thus risk of thrombosis. The thin profile of the deployed tubular member in accordance with the present invention also facilitates more rapid endothelialization of the stent.

The wall of the tubular member comprises at least one module, which consists of a series of sliding and locking radial elements. Preferably, a plurality of modules are connected in the longitudinal axis via linkage elements which couple at least some of the radial elements between adjacent modules. The radial elements are configured within each module so as to define the circumference of the tubular member. Each radial element within a module is preferably a discrete, unitary structure, comprising one or more circumferential ribs bowed in the radial axis to form a fraction of the total circumference of the tubular member. The radial elements within a module are preferably assembled so that all of the circumferential ribs are substantially parallel to one another. At least one of the ribs in each radial element has one or more stops disposed along the length of the rib. At least some of the radial elements also have at least one articulating mechanism for slideably engaging the rib(s) from adjacent, circumferentially offset radial elements. In one aspect of the present invention, the articulating mechanism includes a tab for engaging the stops disposed along the slideably engaged adjacent rib. The articulation between the tab from one radial element and the stops from an adjacent radial element is such that a locking or ratcheting mechanism is formed, whereby the adjacent radial elements may slide circumferentially apart from one another, but are substantially prevented from sliding circumferentially toward one another. Accordingly, the tubular member may be radially expanded from a smaller diameter to a larger diameter, but recoil to a smaller diameter is minimized by the locking mechanism. The amount of recoil can be customized for the application by adjusting the size and the spacing between the stops along the ribs. Preferably, the recoil is less than about 5%.

Some aspects of the present stents are disclosed in U.S. Pat. No. 6,033,436 issued to Steinke, and U.S. application Ser. No. 09/283,800. The disclosures of which are hereby incorporated in their entirety by reference thereto.

Referring to FIGS. 1A–C, a plan view of one module 10 is illustrated comprising a series of sliding and locking radial elements 20 in accordance with one embodiment of the present invention. The pictured module is shown in a two-dimensional, flat plane. Each radial element has one or more elongated ribs 22 (in the vertical axis) with a generally perpendicular end portion 24 (in the horizontal axis), permanently affixed to each end of each rib. Each rib has at least one stop 30. The radial elements in the module alternate from a one-rib configuration 20' to a two-rib configuration 20". The illustrated one-rib configuration 20' has a single rib 22 with a plurality of stops 30, whereas the illustrated two-rib configuration 20" has two ribs, each with a plurality of stops 30. The radial elements in accordance with the invention could have different numbers of circumferential ribs 22, however, vertically adjacent radial elements preferably alternate between an odd-numbered rib configuration and an even-numbered rib configuration, as illustrated in FIGS. 1A–C.

The odd-even alternation in adjacent radial elements facilitates nesting of the circumferential ribs 22 within a module, while maintaining a constant width (w). However, if the radial elements are configured differently, e.g., in a parallelogram shape as opposed to a rectangular shape, wherein the ribs exhibit a non-circumferential orientation, then changes in the longitudinal length of the module would be expected upon expansion of the tubular member. Such variations are encompassed within the present invention.

With reference to FIGS. 1A–C, some of the end portions 24 of the radial elements 20 in the illustrated design are depicted with articulating mechanisms 34 each comprising a slot 36 for slideably engaging a rib from a vertically adjacent radial element and a tab 32 for engaging the stops 30 in the slidably engaged rib. The end portions 24 of the one-rib radial elements 20' are generally adapted to articulate with each rib 22 from the slideably engaged, vertically adjacent two-rib radial element 20". The end portions 24 of the two-rib radial elements 20" are generally adapted to articulate with the single rib 22 of the slideably engaged, vertically adjacent one-rib radial element 20'. The articulating mechanism is shown in greater detail in FIGS. 2A and 2B. The stops 30 may be evenly distributed along the entire length (as shown on the second radial element from the bottom), or the stops may be distributed unevenly along the ribs (as shown in the upper most radial element).

The articulation between the tab 32 from one radial element and the stops 30 from an adjacent radial element creates a locking or ratcheting mechanism, such that only one-way sliding (expansion) can take place. Accordingly, the series of radial elements in plan view, as shown in FIGS. 1A–C, is adjustable from a collapsed state, as shown in FIG. 1A, to a partially expanded state, as shown in FIG. 1B, to a fully expanded state, as shown in FIG. 1C. Expansion of the module 10 in plan view may be accomplished by application of opposing forces (arrows). The nested, sliding and locking radial elements 20 slide apart from one another, thereby increasing the height (h) of the series in the vertical axis, with no change in the width (w) of the series in the horizontal axis. The locking mechanism formed by the articulation between the tab 32 and the individual stops 30 prevents the expanded series from recoiling back to a more collapsed height.

When the module 10 is rolled to form a tubular member, a slideable articulation may be made between the end portion on the radial element on top of the module and the rib from the radial element on the bottom of the module. Likewise, a slideable articulation may also be made between the end portion on the radial element on the bottom of the module and the two ribs from the radial element on top of the module. In a variation, after rolling to form a tubular member, the top and bottom end portions can be connected to one another by a variety of fastening means known in the art, including welding, adhesive bonding, mechanical or snap fit mechanism, etc. In other modes, specialized structural elements may be included to facilitate coupling of the top and bottom portions of the rolled module. Examples, of specialized circumferential coupling elements are detailed below with reference to FIGS. 4A and 4B.

Figure 2A:
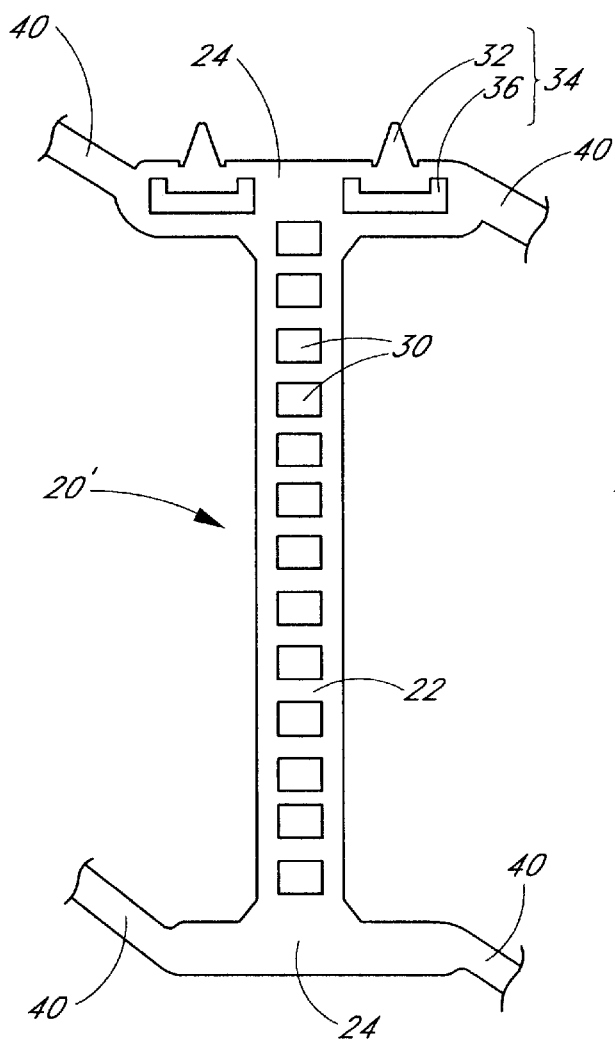
FIGS. 2A and 2B are schematic views of the individual radial elements from FIGS. 1A–C. A one-rib radial element is shown in FIG. 2A and a two-rib radial element is shown in FIG. 2B.
Figure 2B:
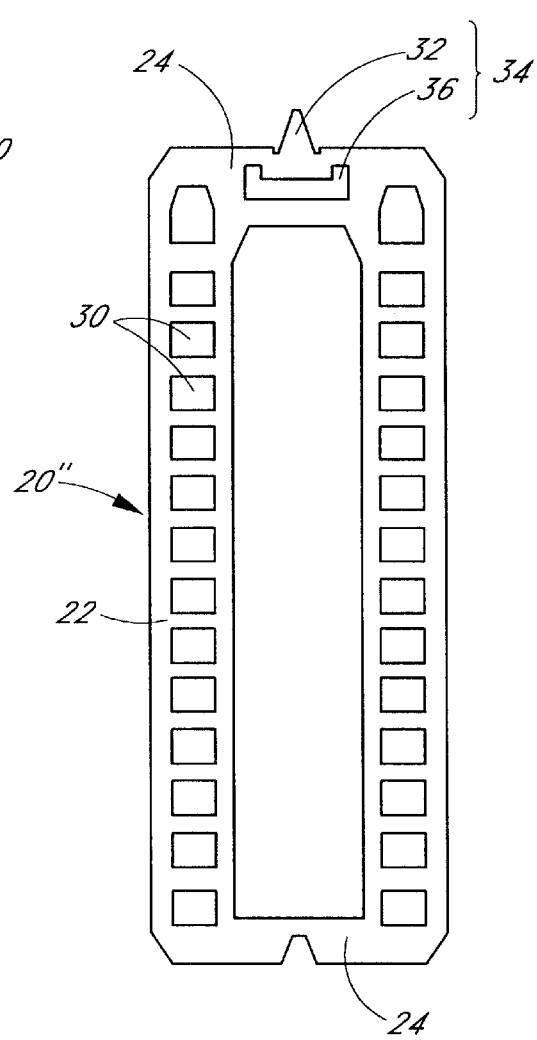

With reference to FIGS. 2A and 2B, individual one-rib 20' and two-rib 20" radial elements, respectively, are shown unassembled in greater detail. Both the one-rib radial element 20' in FIG. 2A and the two-rib 20" radial element in FIG. 2B have at least one circumferential rib 22 and an end portion 24 on each end of the rib. The rib has one or more stops 30 disposed along the length of the rib 22. One end of each of the illustrated radial elements includes an articulating mechanism 34 comprising a tab 32 and a slot 36. Also illustrated in FIGS. 2A and 2B are linkage elements 40, which extend laterally from an end portion 24 of a radial element. These linkage elements 40 are used to couple radial elements between adjacent modules. The linkage elements may extend from either or both end portions 24 of either the one-rib 20' or two-rib 20" radial elements. In one preferred mode (as illustrated), the linkage elements 40 extend off of both end portions 24 of a one-rib radial element 20'. The configuration and angle of the linkage elements may vary substantially depending on the desired linkage distance between modules and the desired flexibility and surface area coverage of the stent.

Figure 3:
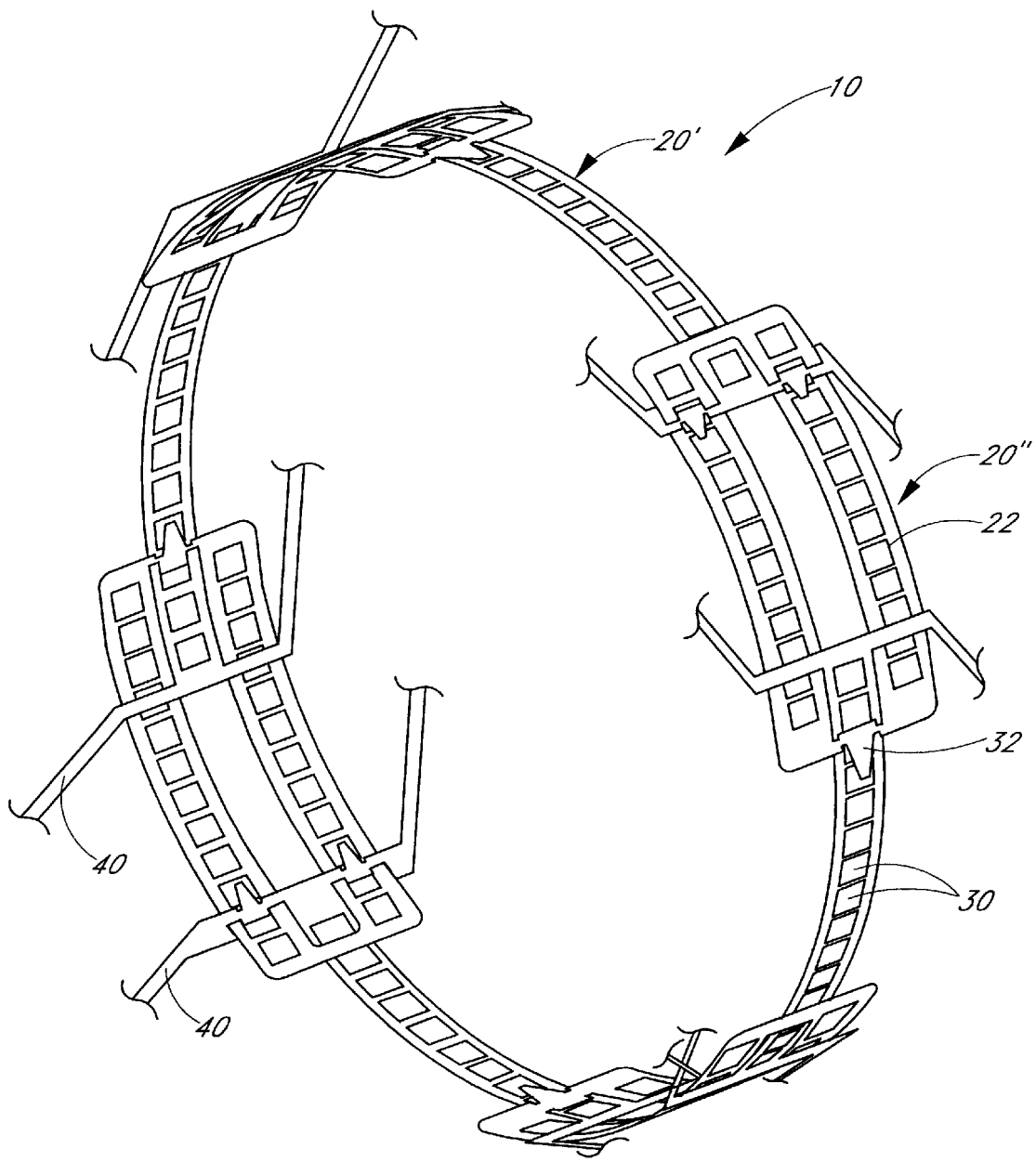
FIG. 3 is a perspective view of a tubular member formed from one module comprising a series of one-rib and two-rib sliding and locking radial elements.

A tubular member formed from a single module 10 comprising four one-rib radial elements 20' and four two-rib radial elements 20", similar to the plan view described with reference to FIGS. 1A–D and FIGS. 2A–B, is shown in FIG. 3. The radial elements that form the wall of the tubular member alternate between radial elements having odd and even-numbers of circumferential ribs 22. Each rib in the illustrated module has one or more stops 30. An articulating mechanism (shown in greater detail in FIGS. 2A and 2B), has a tab 32 that engages the stops and prevents the tubular member from collapsing to a smaller diameter. Each radial element forms a portion of the total circumference of the tubular member (in this case ⅛ of the circumference). Preferably, the total number of radial elements that comprise a module varies between about 2 and 12. More preferably, the number of radial elements is between 4 and 8 radial elements. Linkage elements 40 are shown extending laterally away from the module on both sides. The linkage elements 40 are for coupling the module to similar modules to create a tubular member with a greater longitudinal length.

Figures 4A, 4B:
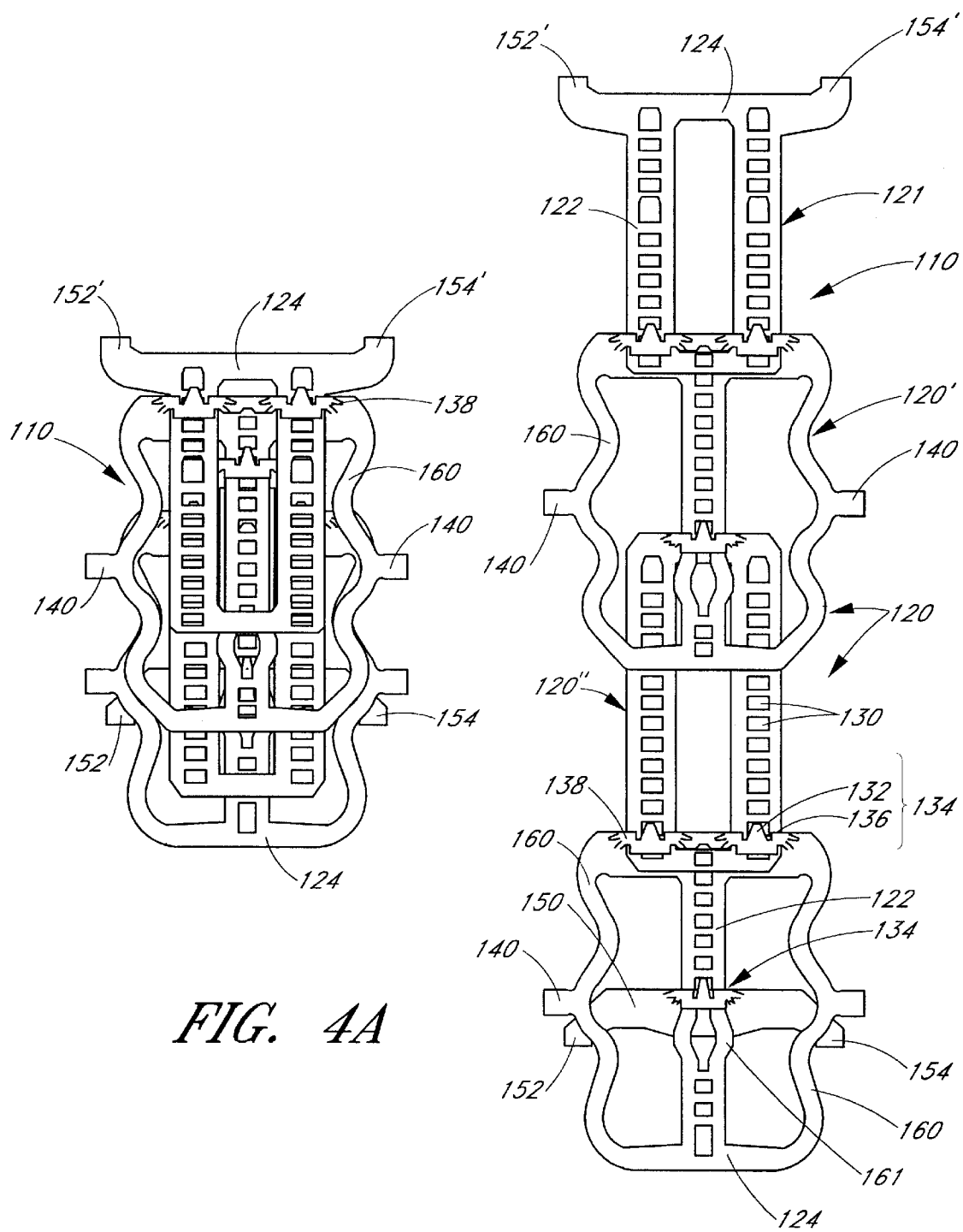
FIGS. 4A and 4B are plan views of another embodiment of a module having a floating coupling element, wherein the one-rib radial elements further comprise a frame element. The module is shown in a collapsed state (FIG. 4A) and an expanded state (FIG. 4B).
Figure 4C:
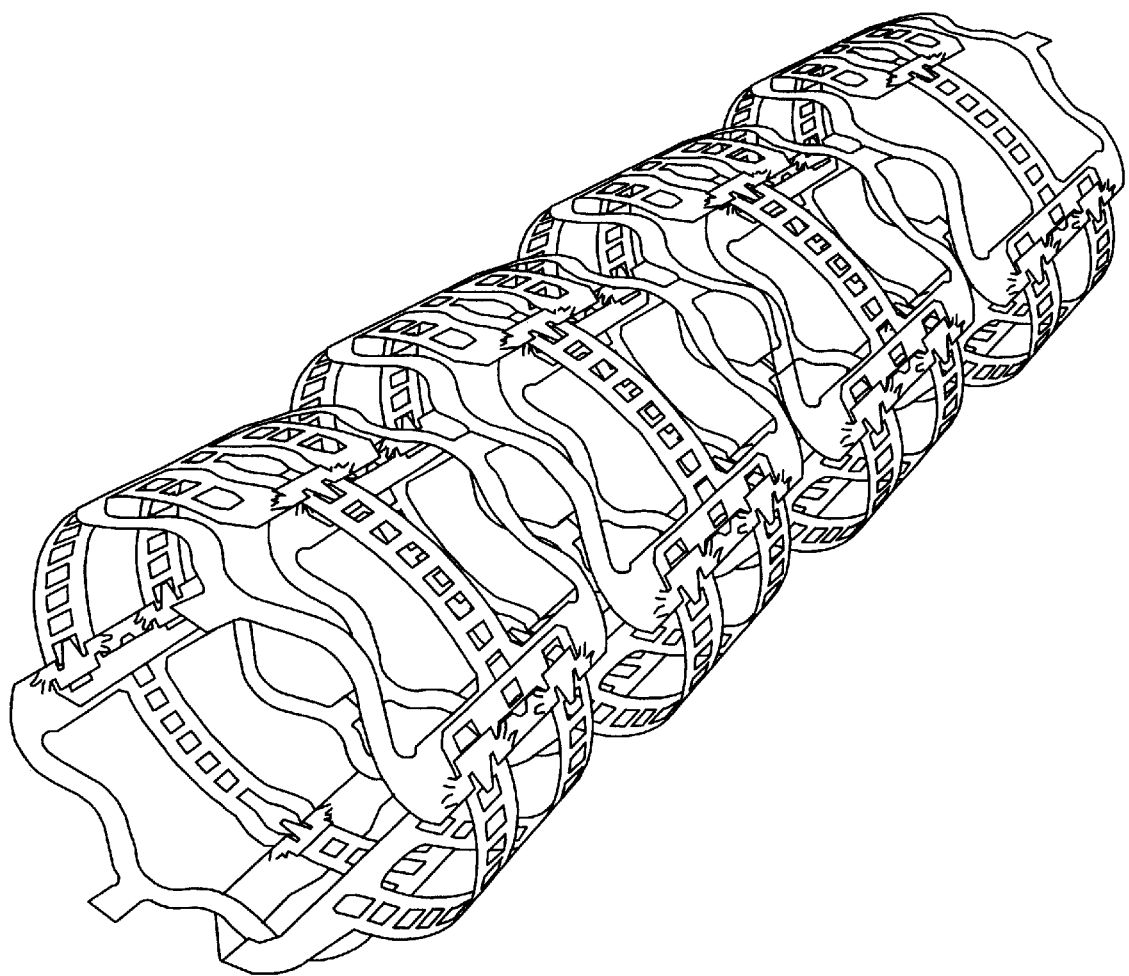
FIG. 4C is a perspective view of a tubular member comprising a plurality of modules shown in FIGS. 4A and 4B.
Figure 4D:
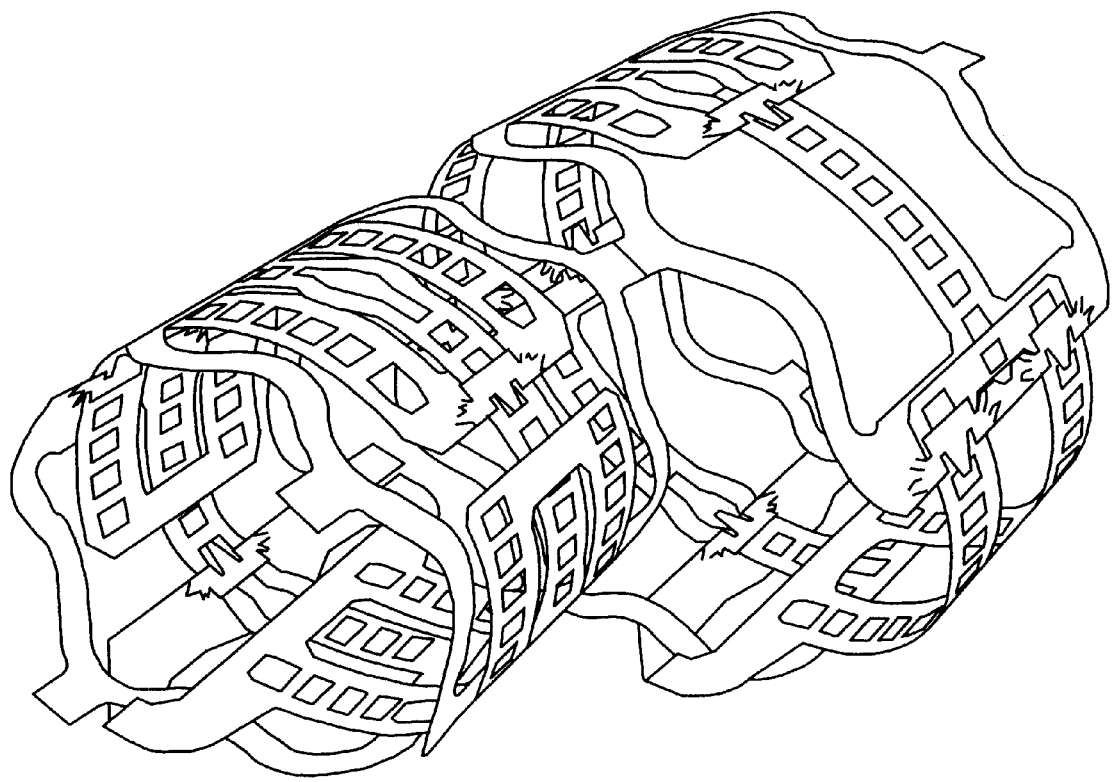
FIG. 4D is a perspective view of a tubular member comprising a plurality of the modules shown in FIGS. 4A and 4B, wherein the expanded diameter of adjacent modules is not the same.

A variation of the basic module design described above with reference to FIGS. 1A–D and FIGS. 2A–B is shown in FIGS. 4A and 4B. The module is illustrated in plan view in both a collapsed state (FIG. 4A) and an expanded state (FIG. 4B). In this variation of the stent, similar to the earlier design, a module 110 comprises a series of sliding and locking radial elements 120. Each radial element has one or more elongated ribs 122 (in the vertical axis) with a substantially perpendicular end portion 124 (in the horizontal axis), permanently affixed to each end of each rib. Each rib has one or more stops 130. The radial elements in the module alternate from a one-rib configuration 120' to a two-rib configuration 120". The one-rib configuration 120' has a single rib 122 with one or more stops 130, whereas the two-rib configuration 120" has two ribs, each with one or more stops 130.

Like the previously described module, the odd-even alternation in adjacent radial elements facilitates nesting of the circumferential ribs 122 within a module, while maintaining a constant width (w). Some of the end portions 124 of the radial elements 120 in the illustrated design are depicted with articulating mechanisms 134 each comprising a slot 136 for slidably engaging a rib from a vertically adjacent radial element and a tab 132 for engaging the stops 130 in the slidably engaged rib. The feathered edges 138 of the articulating mechanisms 134 shown in FIGS. 4A and 4B indicate where the articulating mechanism has been welded onto the end portions 124 of the respective radial elements, thereby creating the slot 136 through which the engaged rib can slide. The end portions 124 of the one-rib radial elements 120' are generally adapted to articulate with each rib 122 from the slideably engaged, vertically adjacent two-rib radial element 120". The end portions 124 of the two-rib radial elements 120" are generally adapted to articulate with the single rib 122 of the slideably engaged, vertically adjacent one-rib radial element 120'. The stops 130 may be evenly distributed along the entire length (as shown), or the stops may be distributed unevenly along the ribs, or there may be only a single stop.

In FIGS. 4A and 4B, a bump 161 is also shown on the one-rib radial elements 120". These bumps can be incorporated along the length of the rib(s) in order to provide a temporary stop. During expansion, the rib with the bump 161 temporarily stops sliding when the bump 161 enters the slot 136 of the articulating mechanism 138. This temporary stop allows other elements to fully expand before the temporary stop is overcome by additional radial expansion force. The incorporation of one or more of these bumps in a module facilitates uniform expansion of the radial elements within the module. In addition or in the alternative to the temporary stop created by the bump 161, some elements may have only one stop so that this element is expanded first to the stop, with the other elements having multiple stops providing preferred expansion steps.

The articulation between the tab 132 from one radial element and the stops 130 from an adjacent radial element creates a locking or ratcheting mechanism, such that only one-way sliding (expansion) can take place. The nested, sliding and locking radial elements 120 slide apart from one another, thereby increasing the height of the series in the vertical axis, with no change in the width of the series in the horizontal axis. The locking mechanism formed by the articulation between the tab 132 and the individual stop(s) 130 prevents the expanded series from recoiling back to a more collapsed height.

The module 110 shown in FIGS. 4A and 4B includes a floating coupling element 150 which is shaped like the end portion 124 of a two-rib radial element 120", having one articulating mechanism 134 adapted to slideably engage the circumferential rib 122 of a one-rib radial element 120'. In variations to the depicted embodiment, the floating coupling element may be adapted to float over more than one rib in radial elements having two or more circumferential ribs. The coupling element 150 is also adapted to couple with the end portion 124 of the top radial element 121 in the series. Both the coupling element 150 and the end portion 124 on the top radial element 121 are configured so as to have coupling arms 152 and 154, and 152' and 154', which may exhibit a complimentary configuration as illustrated.

Another specialization illustrated in FIGS. 4A and 4B, are frame elements 160 from which linkage elements 140 extend laterally away from the frame elements 160. In the module depicted in FIGS. 4A and 4B, the frame elements 160 are only employed on the one-rib radial elements 120'. The frame elements are shown attached to and extending between the end portions 124 of the one-rib radial elements 120', so that the circumferential rib 122 is surrounded, or framed, by the end portions 124 and frame elements 160. The use of frame elements to facilitate coupling between adjacent modules has several advantages. The frame elements contribute additional physical support to the vessel wall. Larger surface area of the individual elements may be desirable in some instances, first to provide greater support for the surrounding lumen, and second the larger surface area provides a larger carrier for site-directed introduction of biologically active agents (discussed below). Alternatively, a smaller surface can be configured to minimize impact of the stent material on the vessel wall, for example, by using narrower ribs and frame elements. By suspending the linkage elements 140 laterally outward from the radial elements, the frame elements minimize the length of the linkage elements 140 that will be necessary to couple adjacent modules, while separating the sliding ribs from one module from those of the adjacent module. Coupling of the linkage elements 140 in adjacent modules provides for a very flexible stent. The flexure is also carried to the frame element 160, allowing much larger movement, and thus, increased flexibility. In variations to this mode, the frame elements can be employed in radial elements have more than one rib. See e.g., FIG. 5, showing a module design comprising a series of two-rib radial elements, each having frame elements.

Figure 5:
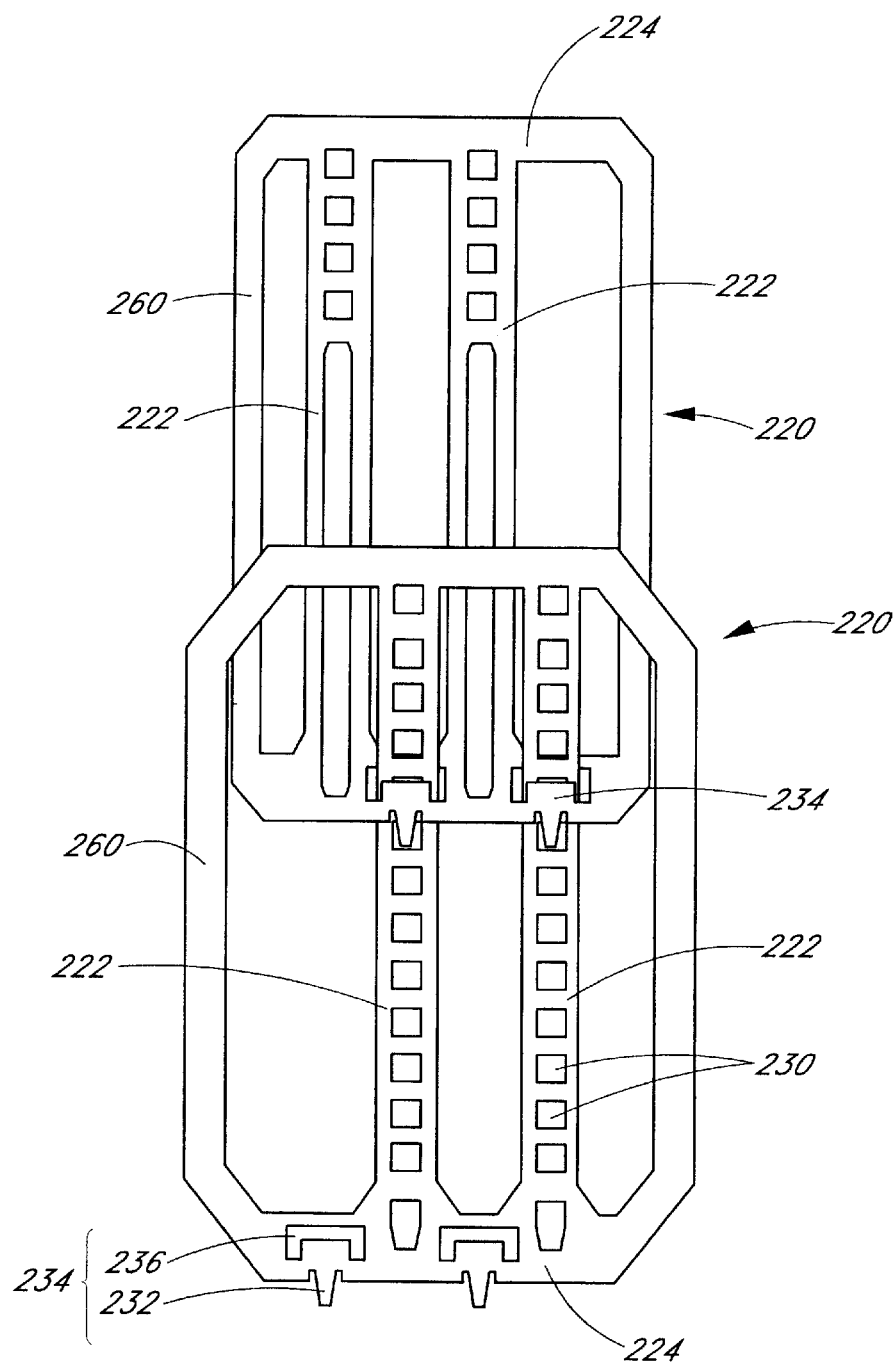
FIG. 5 is a plan view of another embodiment of a module comprising sliding and locking radial elements having two ribs each and a frame element.

With reference to FIG. 5, a variation of odd-even radial elements is shown, wherein each of the two illustrated radial elements 220 have two circumferential ribs 222 and two articulating mechanisms 234 disposed on at least one of the end portions 224 of the radial elements and comprising a tab 232 and a slot 236. As in previous modes of the present invention, the circumferential ribs may have a plurality of stops 230 disposed along the length of the rib. Each of the radial elements has a frame element 260, which is substantially rectangular in shape (linkage elements are not shown). The frame element may be any shape consistent with the function of surrounding the ribs and providing a connection point for coupling the radial elements from one module to those from an adjacent module. Preferably the frame elements permit nesting of the ribs in both collapsed and expanded states, without overlapping stent components, which would increase the thickness of the stent.

Figure 6:
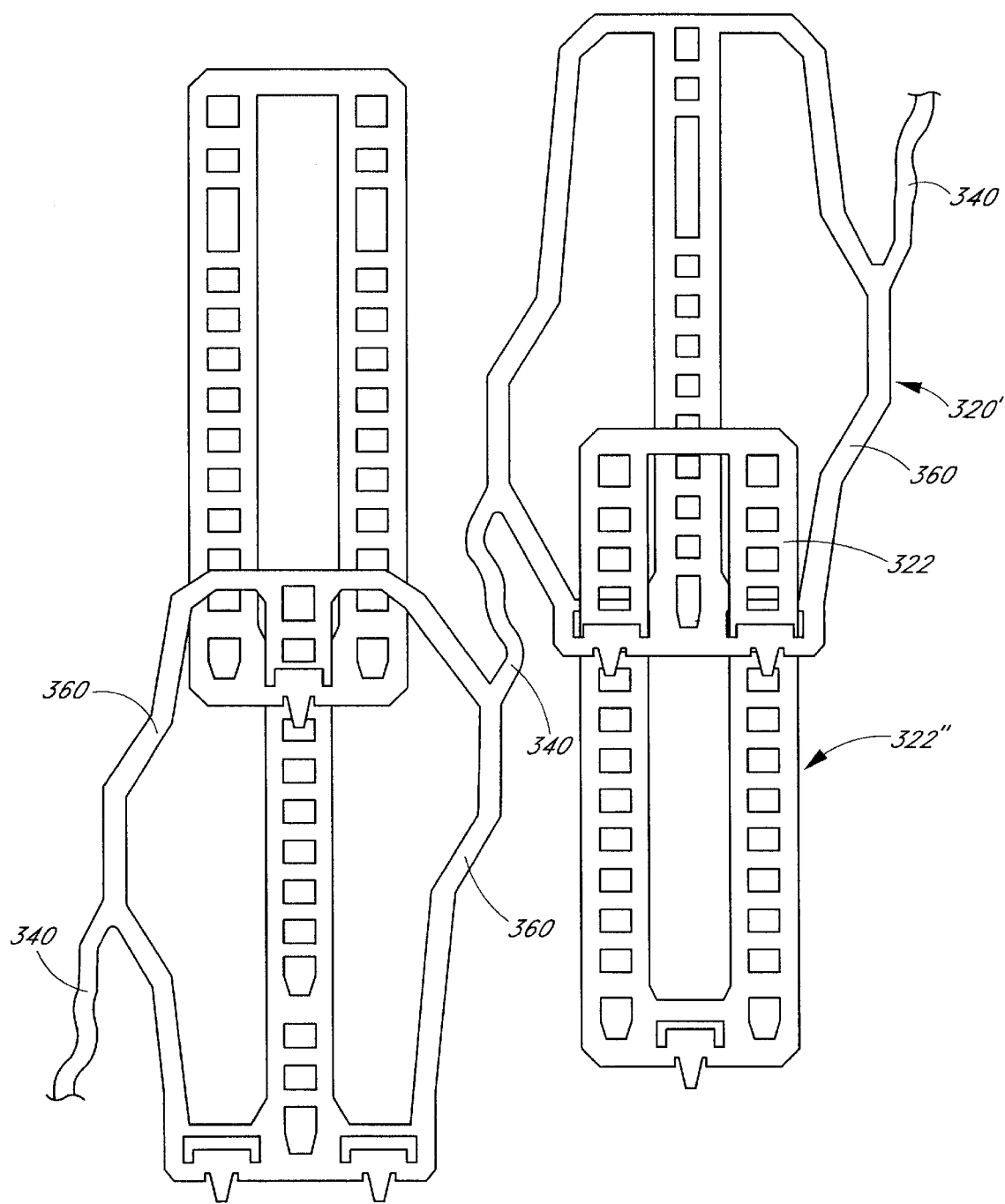
FIG. 6 is a plan view of a variation of the stent showing the linkage of adjacent modules, each comprising alternating one-rib and a two-rib radial elements, wherein the one-rib elements have a frame element adapted to facilitate linkage of adjacent modules in the circumferential axis.

The shape of the frame elements can be varied to cause circumferential off-setting of the different radial elements having odd and even-numbers of ribs. For example, with reference to FIG. 6, the lateral coupling of one pair of radial elements (a one-rib 320' and a two-rib 320" radial element) from one module are connected by the linkage element 340 to another pair of radial elements from an adjacent module. The frame elements 360 are shown in this embodiment surrounding only the one-rib radial elements 320'. The frame elements 360 are configured so as to promote nesting (and not overlap) of ribs 322 and frame elements 360, minimize the lateral space between the modules, and facilitate linkage by a circumferentially, rather than longitudinally, oriented linkage element 340, thereby maximizing the circumferential scaffolding and radial support.

Figure 7:
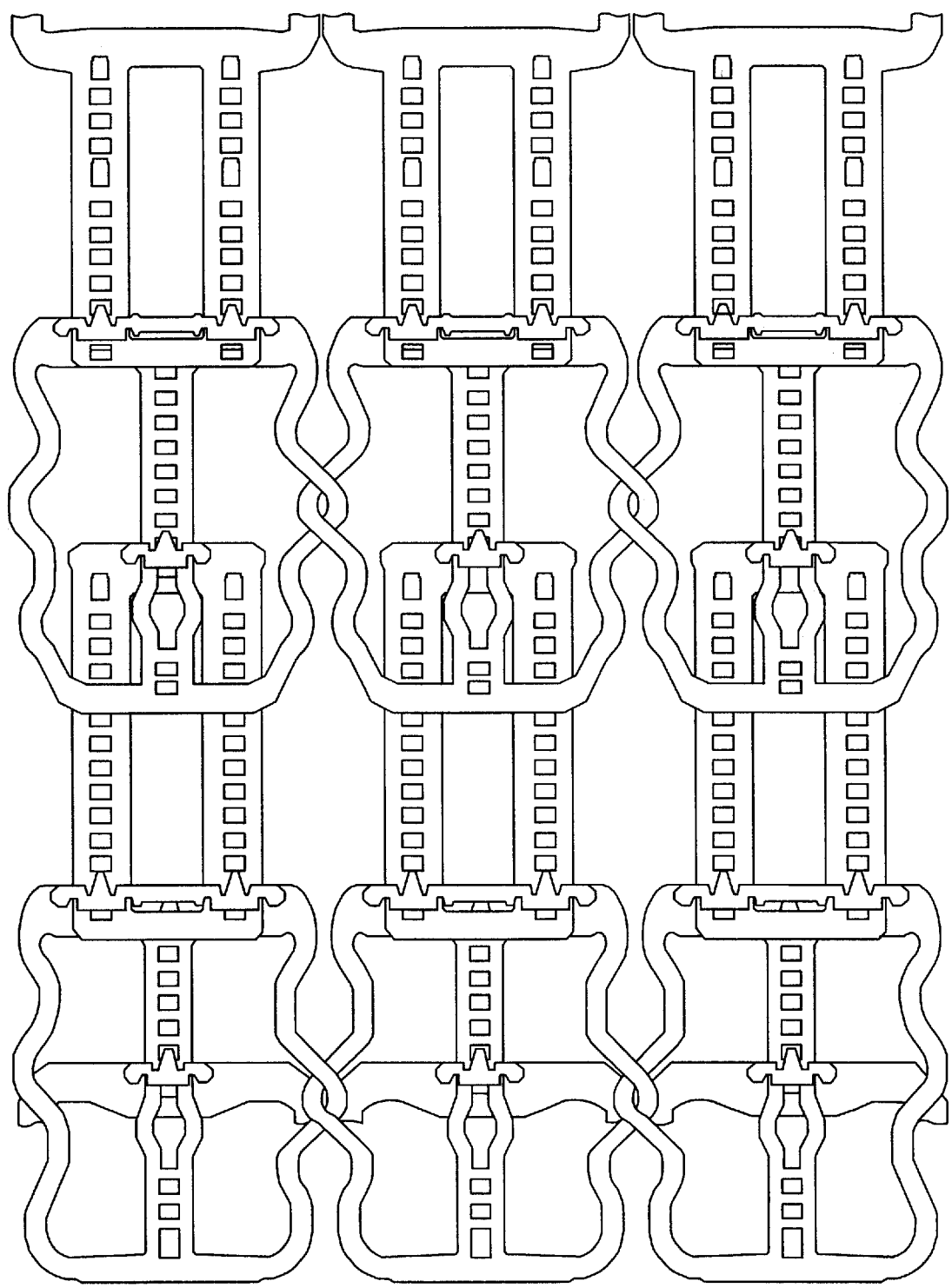
FIG. 7 is a plan view of a variation of the stent showing intermodule coupling through inter-linking of adjacent frame elements.

With reference to FIG. 7, there is illustrated a variation in the coupling mechanism between adjacent modules. No separate linking elements are employed. Instead, the frame elements 360 from adjacent modules may be assembled by weaving so as to inter-link with one another as shown. This coupling between adjacent modules allows much greater stent flexibility.

Figure 8:
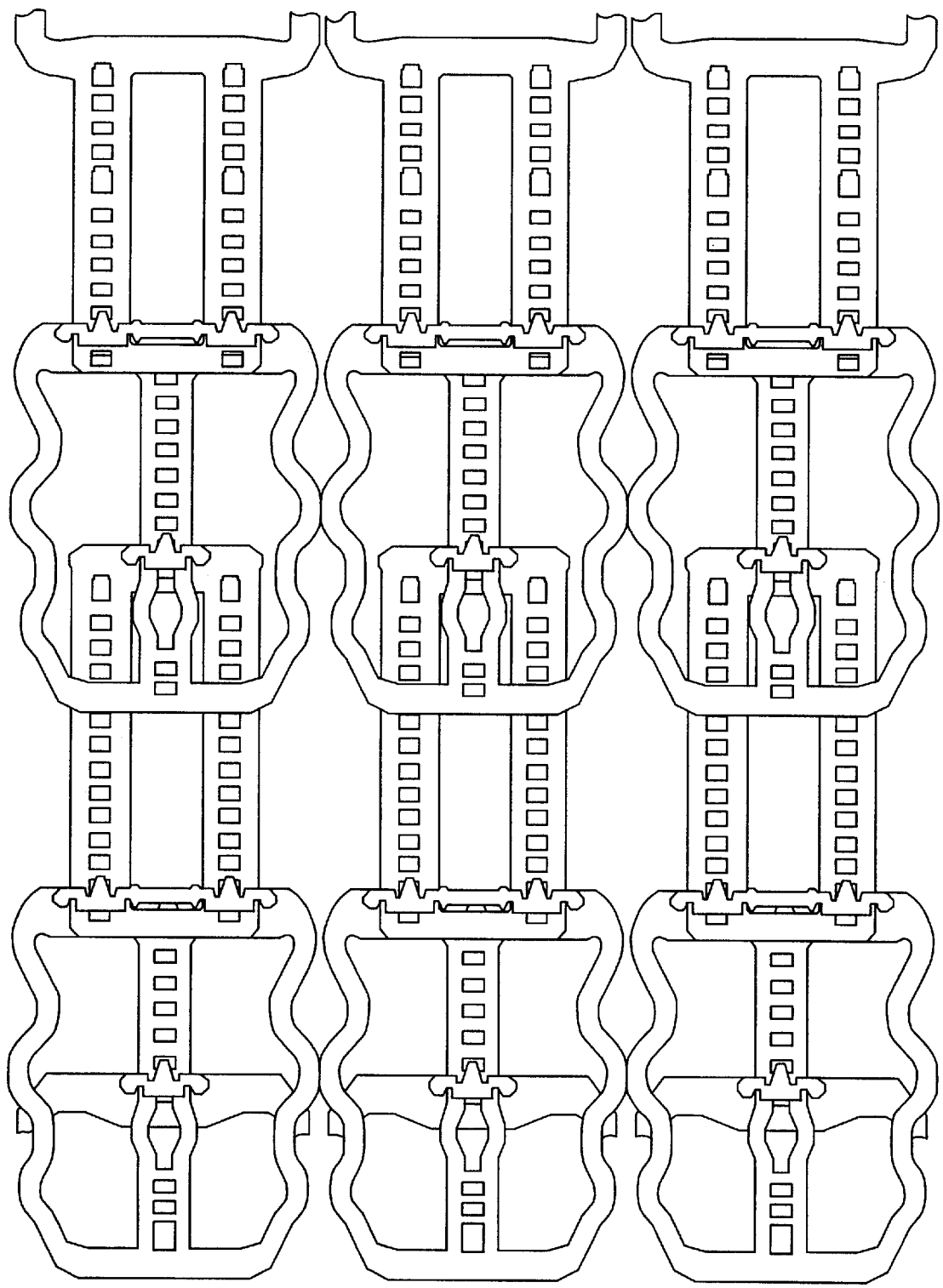
FIG. 8 is a plan view of a variation of the stent showing intermodule coupling through direct attachment of adjacent frame elements to one another.

With reference to FIG. 8, there is illustrated another variation in the coupling mechanism between adjacent modules. No separate linking elements are employed. Instead, the frame elements 360 from adjacent modules are directly joined to one another as shown. The frame elements from adjacent modules may attached by any means suitable for the material, e.g., welding, etc. In one embodiment, frame elements from adjacent modules may be constructed (e.g., cut out) from a single piece of material. This direct coupling of frame elements from adjacent modules tends to produce a stent with greater axial strength.

A variety of different articulating mechanisms and stops are encompassed within the present invention; including but not limited to the slot and tab designs disclosed herein and illustrated in FIGS. 1–8, as well as those disclosed in the parent case, now U.S. Pat. No. 6,033,436 to Steinke, which is incorporated herein in its entirety by reference thereto.

It will be appreciated by those skilled in the art that the basic module design of a series of sliding and locking radial elements provides the manufacturer with a great deal of flexibility with regard to the collapsed and expanded diameters of the stent as well as the longitudinal length. Increased expanded diameter and expansion ratio can be achieved by increasing the number of radial elements within each module. Increased longitudinal length can be achieved by increasing the number of modules that are linked to form the tubular member (from one module as shown in FIG. 9 to six modules as shown in FIG. 10).

Figure 9:
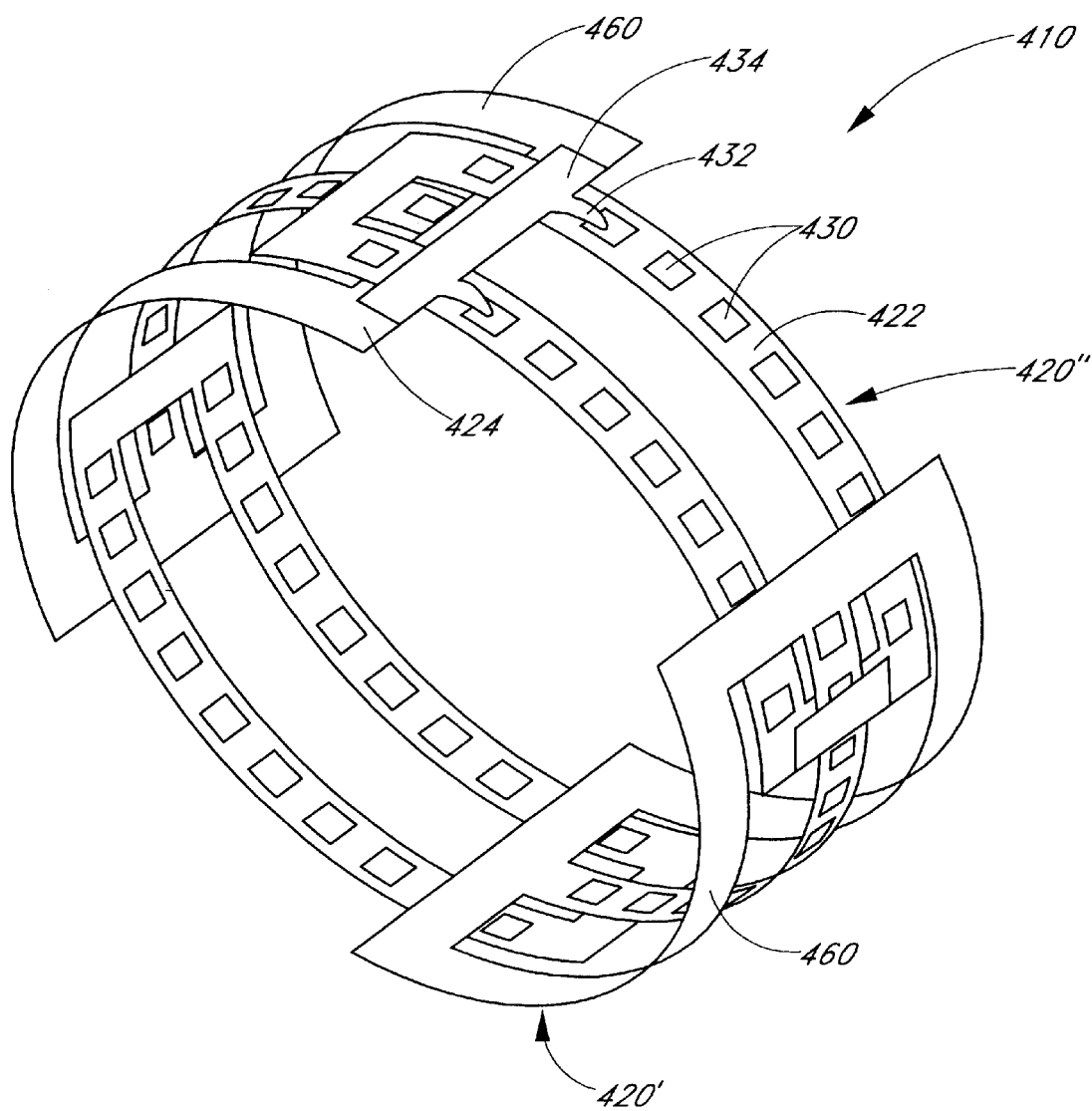
FIG. 9 is a perspective view of a tubular member comprising one module in accordance with one aspect of the present invention.

With reference to FIG. 9, a tubular member having only one module 410 comprising a series of four radial elements (two one-rib radial elements 420' and two two-rib radial elements 420"). In the pictured module 410, no specialized coupling element, like the floating coupling element described with respect to FIGS. 4A and 4B is employed, although such a coupling element could be used in this module without departing from the basic design. The illustrated frame elements 460 have a rectangular shape and surround only the one-rib radial elements 420'. The module shown in FIG. 9 is in an expanded state and is subject to only minimum recoil or collapse (<about 5%) because of the ratcheting effect created by the articulation between a tab 432 on the articulating mechanism 434 of one radial element and a stop 430 on the slideably engaged rib 422 from the adjacent radial element. The articulating mechanism is shown as a separate structural element that has been affixed, e.g., by welding, to the end portion 424 of the respective radial element, thereby entrapping and slideably engaging the rib(s) from the adjacent radial element.

Figure 10:
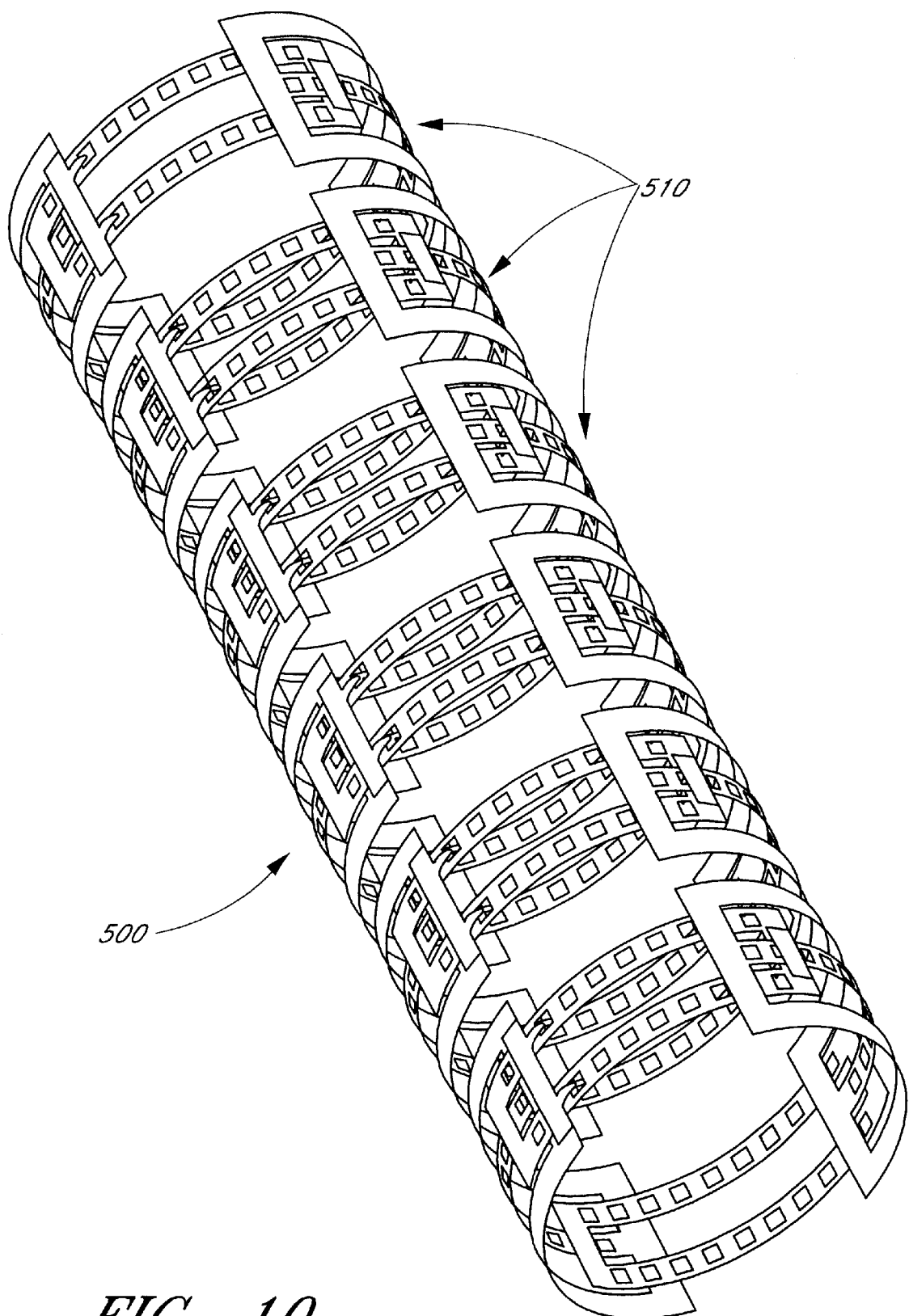
FIG. 10 is a perspective view of a tubular member comprising a plurality of modules.

In FIG. 10, a stent in accordance with the present invention is shown, comprising a tubular member 500 having six modules 510 which are linked in the longitudinal axis (for clarity, linkage elements extending between the frame elements in adjacent modules are not shown).

Figure 11:
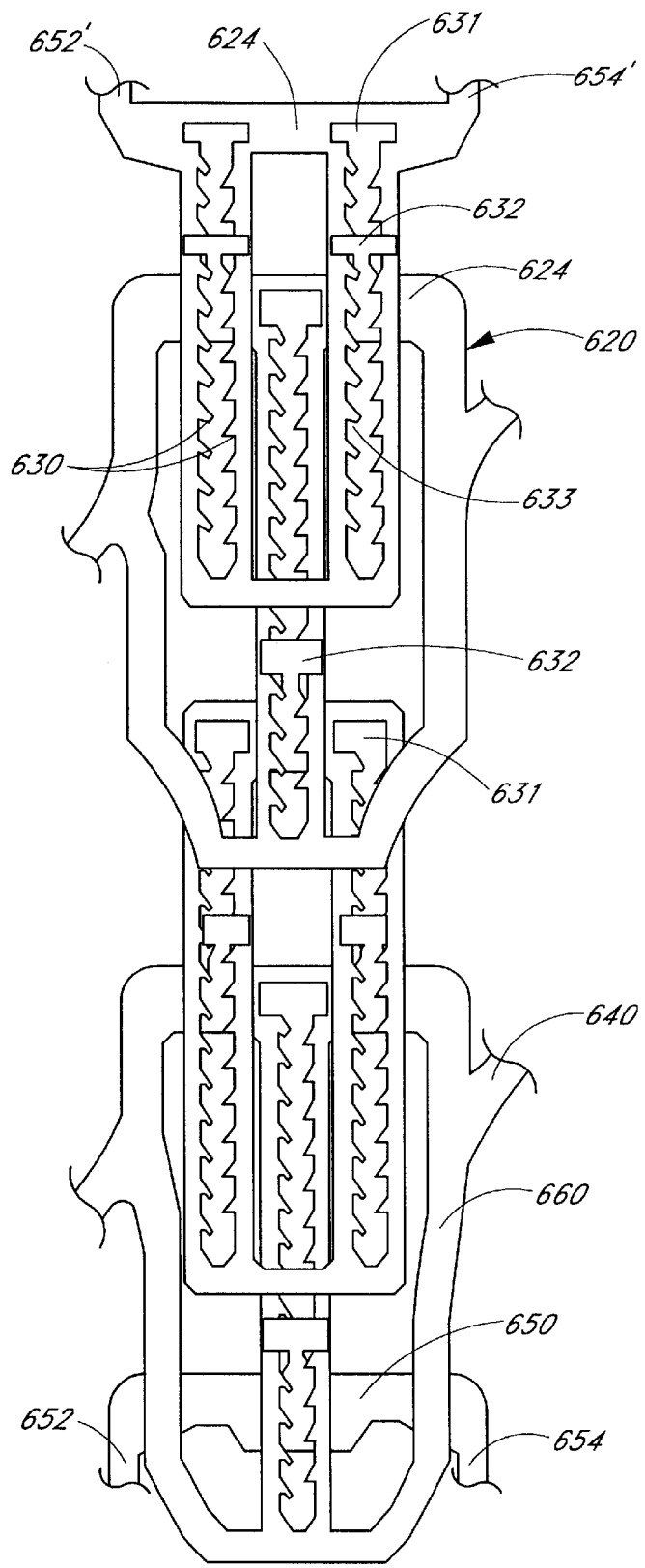
FIG. 11 is a plan view of a snap-together variation of the module design, having a floating coupling element and frame elements on the one-rib radial elements.

In another variation of the present invention, a series of radial elements are illustrated in FIG. 11, wherein the articulating mechanism is formed by a tab 632 in a one-way locking slot 633. This design eliminates the need to attach an overlapping articulating mechanism, e.g., by welding, to entrap and slideably engage a circumferential rib from an adjacent radial element. As shown in FIG. 11, an entry slot 631 is provided at one end of the central locking slot 633, which is disposed along at least a portion of the length of each rib in each radial element. The entry slot 631 is adapted to permit a tab 632 on the end portion 624 of one radial element 620 to fit into and engage the locking slot 633 in the rib. Once the tab(s) 632 is placed through the entry slot(s) 631 the radial elements 620 can be slid apart enough to prevent the tab 632 from coming back out of the entry slot 631. The locking slot 633 is adapted to allow the tab to slide through the slot in only one direction (to a more expanded configuration). For example, as illustrated, the locking slot 633 has a series of serrated notches or stops 630, which are offset on both sides of the slot and which permit the tab 632 to move through the slot 633 in one direction, but which are shaped so as to engage the tab and prevent it from moving through the slot in the opposite direction, i.e., prevent collapse of the expanded stent. Any of a variety of locking slot and stop configurations are encompassed within this snap-together design. Some alternative locking slot and stop configurations are disclosed in the parent application, now U.S. Pat. No. 6,033,436 to Steinke.

The weldless design module illustrated in FIG. 11 is shown with framing elements 660 with linkage elements 640 around the one-rib radial elements and a floating coupling element 650 with coupling arms 652 and 654 for mating with complementary coupling arms 652' and 654' on the end portion 624 of the top radial element in the series. Because the intermodule coupling can be made to the frame elements this increased length allows the stent to be very flexible both in the collapsed and expanded states.

Another variation of the present invention includes varying the articulating mechanism and rib configurations so as to produce increasing friction with progressive expansion. This variation may facilitate uniform expansion of all radial elements within a module.

In another variation of the present stent, different modules within the stent may exhibit different expanded diameters, such that the stent may be adjustable to different luminal states along the length of the stent. Accordingly, the stent may exhibit a tapered configuration in its deployed state, having a larger diameter at one end with progressive or step-wise decreases in modular expanded diameter moving toward the other end of the stent.

It will be appreciated by those of skill in the art that the interlocking and sliding radial element design of the present invention provides the manufacturer with substantial flexibility in customizing the stent for different applications. Because overlap of stent components is minimized by the nesting of ribs and frame elements, the collapsed profile can be very thin without compromising radial strength. Moreover, the degree of overlap does not change substantially during expansion, unlike jelly-roll designs which expand by unraveling of a rolled sheet. Furthermore, the deployment flexibility of the present stent can be customized by changing the length, configuration and number of lateral linkage elements employed. Thus, a very flexible and ultra-thin embodiment of the present stent is deemed to be uniquely suited from deployment in small and difficult to reach vessels, such as the intercranial vessels distal to the carotids and remote coronary vessels.

In another variation, the stent may be used in combination with a covering or sheath to provide a vessel graft, for example, in the treatment of an aneurysm. Materials and methods of making vessel grafts (stent and sheath) incorporating the present stent design are described in detail below.

Figure 12A:
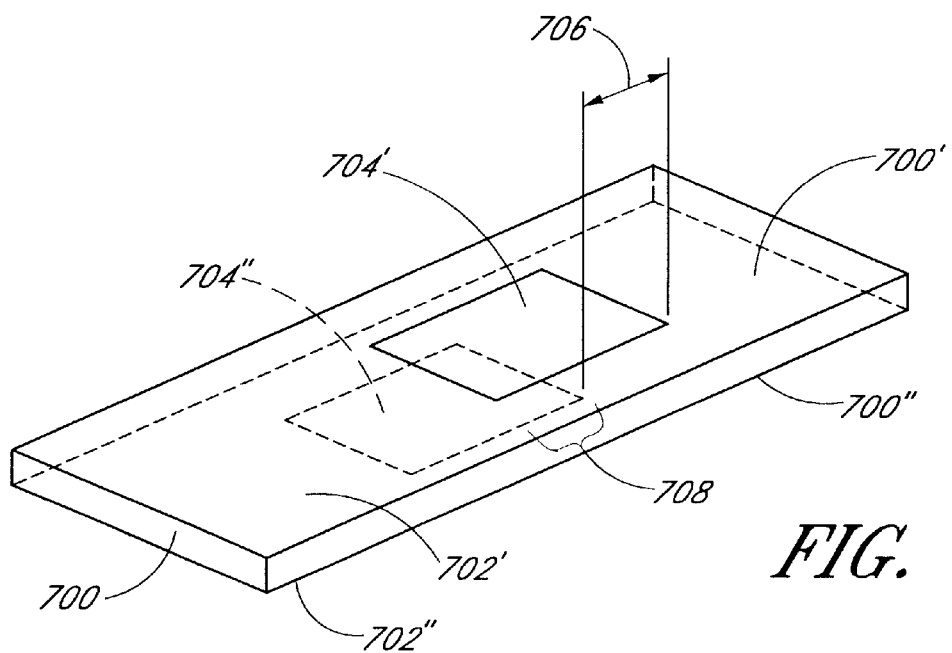
FIGS. 12A–C are perspective views showing the steps in forming a biased or chamfered stop.
Figure 12B:
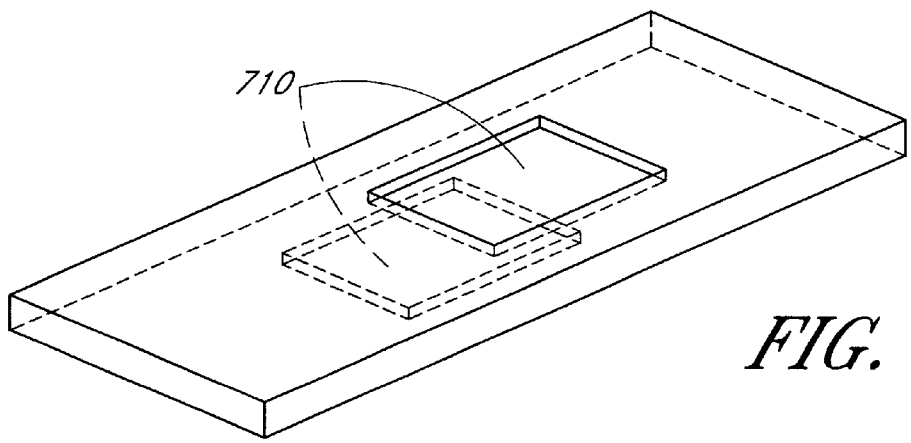
Figure 12C:
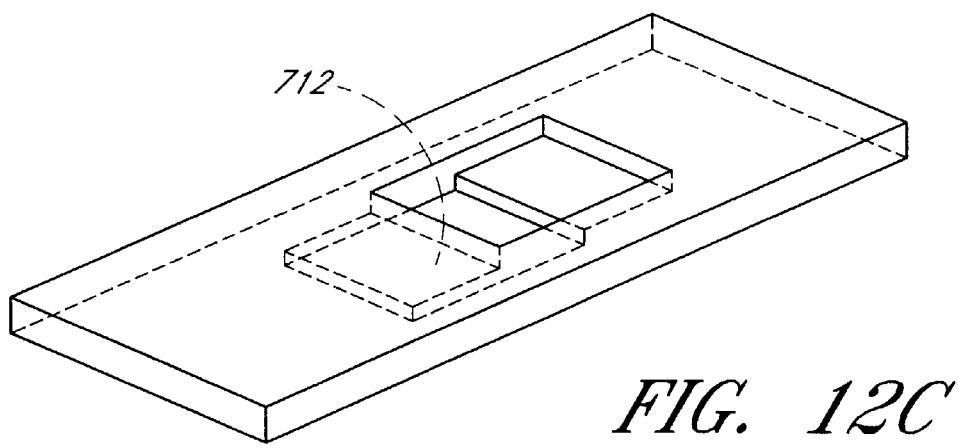

In another variation of the present invention, the stops that are disposed along an elongate rib may be shaped so as to facilitate locking of the tab from the articulating member within the stop, wherein the shape of the hole is adapted to provide a channel which will have a bias for capturing parts (i.e., a tab) sliding past it. With reference to FIGS. 12A–C, there are illustrated the steps in forming one embodiment of such a stop. In FIG. 12A, the stent component 700 can be etched from the top 700' and bottom 700" surfaces. The top and bottom surfaces are coated or masked in some areas 702' and 702", respectively, with a layer that resists etching (e.g., by chemical, laser, etc.), leaving uncoated areas 704' and 704" on the top and bottom, respectively, susceptible to etching. The uncoated areas are offset by a distance 706, which allows some overlap 708 between the top and bottom uncoated areas 704' and 704". As illustrated in FIG. 12B, during the etching process wherein stent material is removed, the uncoated areas 704' and 704" become cavities 710 extending through the stent material. At some point during the etching process, as shown in FIG. 12C, the cavities meet in the overlap area 708 and create a through hole or channel 712. The stop thus formed has a chamfered edge that is biased for capturing a tab as it slides over the stop.

Figure 13A:
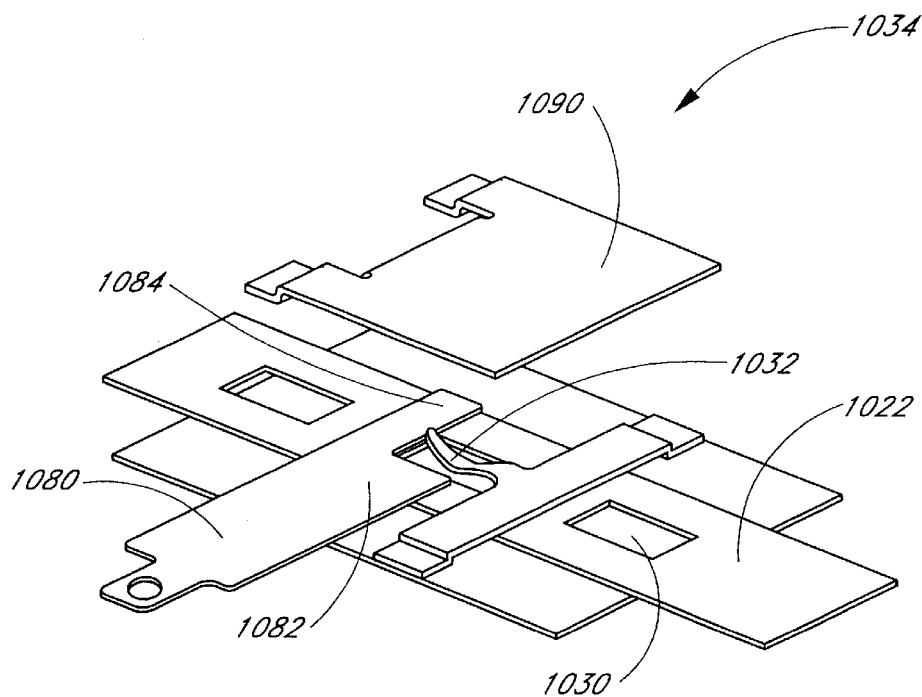
FIGS. 13A and 13B show a releasable articulating mechanism in accordance with a collapsible variation of the present stent. An exploded view of the components of the releasable articulating mechanism is shown in FIG. 13A. A perspective view of several releasable articulating mechanisms positioned on a module are shown in FIG. 13B.

In another embodiment of the present stent, the locking mechanism may be designed to be releasable, wherein the stent may be collapsed for removal from the body lumen. Whereas the other configurations in this disclosure are designed for permanent locking of the members in the expanded state, there may be a need for a reversible, or unlocking mechanism. The components of one possible release mechanism are illustrated in exploded view in FIG. 13A. Most aspects of the stent in accordance with the present invention remain as described in preceding sections. However, the articulating mechanism 1034 is altered to be releasable. The tab 1032 is preformed or biased (as a result of its springy material and/or angle of deployment) not to lockably engage the individual stops 1030. Instead, a moveable slider 1080 and retainer plate 1090 are positioned over the tab 1032 to deflect the tab downward into the individual stops. The shape of tab 1032 which is deflected against the rib 1022 by the slider 1080 and retainer plate 1090 provides locking of rib 1022 against one direction of travel (collapse) while allowing travel in the opposite direction (expansion). The slider 1080 has a wide area 1082 that provides the structural interference to flex tab 1032 into the locking position. When the wide region 1082 is positioned between retainer 1090 and tab 1032 the tab is forced against the slideably engaged rib 1022 and into the passing stops 1030 as the rib slides through the articulating mechanism. The slider 1080 also has a narrow region 1084 that will permit tab 1032 to relax and pull out of the stop 1030. By pulling the slider 1080 outward from the perpendicular plane of the ribs 1020 the narrow region 1084 is repositioned over the tab 1032, thereby allowing the tab to disengage from the stop 1030 and spring back upward against the retainer plate 1090.

Figure 13B:
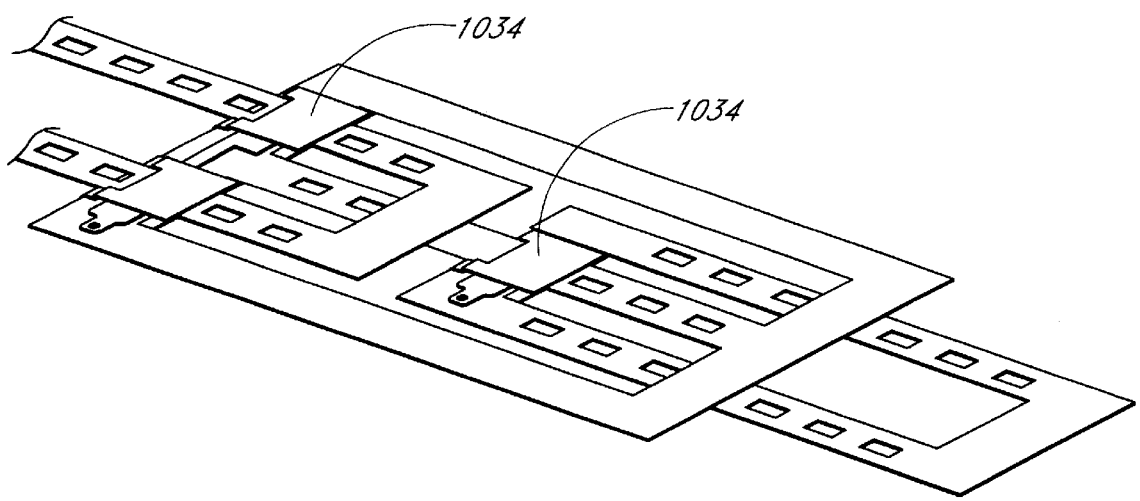

With reference to FIG. 13B there is illustrated a partial view of a module having one-rib and two-rib radial elements and releasable articulating mechanisms 1034. The releasable articulating mechanisms on the one-rib radial element are shown engaging the two ribs from the adjacent two-rib radial element. The slider may be modified on this releasable articulating mechanism to have two narrow regions for releasing both tabs by pulling the one side of the slider.

Stent Manufacture

Preferred materials for the making the stents of the present invention include 316 stainless steel, tantalum, titanium, tungsten, gold, platium, iridium, rhodium and alloys thereof. Also shape memory alloys such as Nitinol may be used in accordance with the present invention. Preferably, sheets are work-hardened prior to forming of the individual stent elements to increase strength. Methods of work hardening are well known in the art. Sheets are rolled under tension, annealed under heat and then re-worked. This may be continued until the desired modulus of hardness is obtained. Most stents in commercial use today employ 0% to 10% work hardened material in order to allow for "softer" material to deform to a larger diameter. In contrast, because expansion of the sliding and locking radial elements in accordance with the present invention depends on sliding rather than material deformation, it is preferred to use harder materials, preferably in the range of about 25–95% work hardened material to allow for thinner stent thickness. More preferably, the stent materials are 50–90% work hardened and most preferably, the materials are 80–85% work hardened.

Preferred methods of forming the individual elements from the metal sheets may be laser cutting, laser ablation, die-cutting, chemical etching, plasma etching or other methods known in the art which are capable of producing high-resolution components. The method of manufacture, in some embodiments, depends on the material used to form the stent. Chemical etching provides high-resolution components at relatively low price, particularly in comparison to high cost of competitive product laser cutting. Tack-welding, adhesives, mechanical attachment (snap-together), and other art-recognized methods of attachment, may be used to fasten the individual elements. Some methods allow for different front and back etch artwork, which could result in chamfered edges, which may be desirable to help improve engagements of lockouts.

In one preferred mode of the present invention, the stent is made, at least in part, from a polymeric material, which may be degradable. The motivation for using a degradable stent is that the mechanical support of a stent may only be necessary for several weeks after angioplasty, particularly if it also controls restenosis and thrombosis by delivering pharmacologic agents. Degradable polymeric stent materials are well suited for drug delivery.

It is believed that there is a need for short-term intervention since the majority of cardiac events occur in the first 6 months, including in-stent restenosis. The permanency of metal stents presents long-term risks and complications. With long lesions and full coverage, metal stents can also preclude surgical re-intervention. The ideal implant: (1) mimics the tissue it is designed to replace in size, shape, and material consistency; (2) neither is disposed to infection nor evokes a foreign body response; (3) is a temporary prosthesis that takes on characteristics of the natural tissue as it disappears; and (4) is a biocompatible implant that has a smooth surface to minimize the risk for thrombus formation and macrophage enzyme activity.

Degradable stents have the potential to perform more like an ideal implant. Degradable stents that integrate seamlessly with the living host tissue may improve tissue biocompatibility due to their temporary residence. With the initial strength to secure the diseased tissue, such stents may eliminate the concern for product migration over time and long-term product failure. They may also minimize time, costs, and complications associated with re-intervention of specific and neighboring sites. Degradable stents have a clear advantage over metal stents in that they can dose the diseased tissue with a drug; compared to drug coated metal stents, degradable stents can dose the tissue over a longer period of time.

Unlike restenosis after angioplasty, in-stent restenosis is a consequence almost entirely of tissue hyperplasia, occurring principally at the points where the stent's struts impinge upon the artery wall. Placement of an excessively stiff stent against the compliant vessel creates a mismatch in mechanical behavior that results in continuous lateral expansile stress on the arterial wall. This stress can promote thrombosis, arterial wall thinning, or excessive cellular proliferation. Hence, polymeric biomaterials, which are more flexible, may minimize the pathology and are more likely to approximate the mechanical profile of the native tissue.

The intact internal elastic lamina (IEL) of a healthy artery serves as an effective barrier to (1) protect the underlying smooth muscle cells (SMC) from exposure to mitogens that induce hyperplasia, and (2) prevent exposure to monocytes or lipid-filled macrophages and circulating elastin peptides that promote hard plaque formation and narrowing of the artery. A biomaterial stent may minimize progression of disease states by mimicking the barrier functions of the IEL: (1) by delivering a cell-cycle inhibitor to counteract the affects of mitogens, and (2) by serving as a temporary physical barrier to the trafficking immune cells.

In the natural disease states, arteriostenosis and atherosclerosis, arteries can have a compromised or structurally discontinuous IEL. The cause of the discontinuity is largely unknown. Elastases, circulating elastin peptides, and elastin receptors may play a pivotal role along with denudation of the endothelium. A biomaterial stent that does not grossly over expand the vessel wall may minimize the risk for further perforation of the IEL. In addition the stent surface can serve as an anchorage site for formation of an endothelial lining, the gatekeeper to blood elements and circulating molecules.

In one mode of the degradable stent of the present invention, the stent matrix may be formulated so as to release a pharmacologic agent. Mechanical treatment of diseased vessels by angioplasty and stenting can further damage the arterial wall. Ironically, each of these practices can promote thrombus formation and restenosis associated with reocclusion within 6- to 24-months post-operatively. These inadequate clinical outcomes are the impetus for development of many counteractive therapies. Some new treatments for restenosis are use of radioisotopes, Paclitaxel and Rapamycin, all of which inhibit vascular cell proliferation. Alternatively, the stent may be mounted onto a catheter that holds the stent as it is It is estimated that pharmacological interventions for restenosis need to occur continuously for 2–4 weeks following angioplasty or stent implantation. It is also estimated that a polymer stent can deliver a drug dose that is ten times higher than systemic delivery. If a cell cycle inhibitor was released from a degradable stent, we may achieve optimal long-term patency in the diseased vessel.

Degradable biomaterial stents may improve the long-term product safety and efficacy for the patients. We believe that a completely degradable, drug-eluting stent that resides in the vessel for several weeks after deployment will be effective in controlling restenosis. Accordingly, the present invention encompasses stents having the sliding and locking geometry described above, wherein the stent components are made from a functional biomaterial.

The mechanical properties of the degradable biomaterial are selected in accordance with the present invention to exhibit at least one, and preferably more, of the following characteristics: (1) resist failure due to the multiaxial stress-strain behavior of native arteries and exceeds that of annealed metals, which are known to fail for stent applications; (2) retain mechanical strength during several weeks or months post-deployment; (3) degrade via hydrolytic or enzymatic degradation preferably with surface erosion whereby the implant degrades uniformly and maintains its original shape as it degrades; (4) maintains favorable hemodynamics; (5) exhibits a hydrophilic, negatively charged, smooth and uniform surface with a low critical surface tension; (6) supports endothelialization; (7) is nontoxic and eliminated from the body safely, i.e., no systemic effects; and (8) includes an anti-restenosis pharmacological agent. The pharmacologic agent may be a cell-cycle inhibitor that inhibits SMC proliferation, allows for favorable early and late remodeling, and that is stable in the biomaterial. The degradable biomaterial and pharmacologic agent preferably provide dosing of the lesion for about three to four weeks or through the degradation cycle of stent.

Degradable plastic or natural (animal, plant or microbial) or recombinant materials in accordance with one aspect of the present invention may include polydepsipeptides, nylon copolymides, conventional poly(amino acid) synthetic polymers, pseudo-poly(amino acids), aliphatic polyesters, such as polyglycolic acid (PGA), polylactic acid (PLA), polyalkylene succinates, polyhydroxybutyrate (PHB), polybutylene diglycolate, and poly epsilon-caprolactone (PCL), polydihydropyrans, polyphosphazenes, polyorthoesters, polycyanoacrylates, polyanhydrides, polyketals, polyacetals, poly($\alpha$-hydroxy-esters), poly(carbonates), poly (imino-carbonates), poly($\beta$-hydroxy-esters), polypeptides, and their chemical modifications and combinations (blends and copolymers) and many other degradable materials known in the art. (See e.g., Atala, A., Mooney, D. Synthetic Biodegradable Polymer Scaffolds. 1997 Birkhauser, Boston; incorporated herein by reference).

In one preferred mode, the degradable materials are selected from the group consisting of poly(alkylene oxalates), polyalkanotes, polyamides, polyaspartimic acid, polyglutarunic acid polymer, poly-p-diaxanone (e.g., PDS from Ethicon), polyphosphazene, and polyurethane.

In a more preferred mode, the degradable materials are selected from the group consisting of poly(glycolide-trimethylene carbonate); terpolymer (copolymers of glycolide, lactide or dimethyltrimethylene carbonate); polyhydroxyalkanoates (PHA); polyhydroxybutyrate (PHB) and poly(hydroxybutyrate-co-valerate) (PHB-co-HV) and copolymer of same; poly(epsilon-caprolactone) and copolymers (e.g., lactide or glycolide); poly(epsilon-caprolactone-dimethyltrimethylene carbonate); polyglycolic acid (PGA); and poly-L and poly-D(lactic acid) and copolymers and additives (e.g., calcium phosphate glass) and lactic acid/ethylene glycol copolymers.

In a most preferred mode, the degradable materials are selected from the group consisting of polyarylates (L-tyrosine-derived) or free acid polyarylates, polycarbonates (L-tyrosine-derived), poly(ester-amides), poly (propylene fumarate-co-ethylene glycol) copolymer (i.e., fumarate anhydrides), polyanhydride esters (mechanically stronger) and polyanhydrides (mechanically weaker), polyorthoesters, ProLastin or silk-elastin polymers (SELP), calcium phosphate (BIOGLASS), magnesium alloys, and a composition of PLA, PCL, PGA ester commercial polymers used sigularly or in any mixture.

Natural polymers (biopolymers) include any protein or peptide. These can be used in a blend or copolymer with any of the other aforementioned degradable materials, as well as with pharmacologic substances, or with hydrogels, or alone. Typically, these biopolymers degrade upon the action of enzymes. Preferred biopolymers may be selected from the group consisting of aliginate, cellulose and ester, chitosan NOCC and NOOC-G), collagen, cotton, dextran, elastin, fibrin, gelatin, hyaluronic acid, hydroxyapatite, spider silk, other polypeptides and proteins, and any combinations thereof.

Coatings for degradable and metal stent materials may be selected from the group consisting of hydrogels, such as: NO-carboxymethyl chitosan NOCC), PEG diacrylate with drug (intimal layer) with second layer without drug (blood flow contact), polyethylene oxide, polyvinylalcohol (PVA), PE-oxide, polyvinylpyrolidone (PVP), polyglutarunic acid polymers, DMSO or alcohols and any combinations thereof.

Where plastic and/or degradable materials are used, the elements may be made using hot-stamp embossing to generate the parts and heat-staking to attach the linkage elements and coupling arms. Other preferred methods comprise laser ablation using a screen, stencil or mask; solvent casting; forming by stamping, embossing, compression molding, centripital spin casting and molding; extrusion and cutting, three-dimensional rapid prototyping using solid free-form fabrication technology, stereolithography, selective laser sintering, or the like; etching techniques comprising plasma etching; textile manufacturing methods comprising felting, knitting, or weaving; molding techniques comprising fused deposition modeling, injection molding, room temperature vulcanized (RTV) molding, or silicone rubber molding; casting techniques comprising casting with solvents, direct shell production casting, investment casting, pressure die casting, resin injection, resin processing electroforming, or reaction injection molding (RIM). These parts may be connected or attached by solvent or thermal bonding, or by mechanical attachment. Preferred methods of bonding comprise the use of ultrasonic radiofrequency or other thermal methods, and by solvents or adhesives or ultraviolet curing processes or photoreactive processes. The elements may be rolled by thermal forming, cold forming, solvent weakening forming and evaporation, or by preforming parts before linking. Soluble materials such as hydrogels which are hydrolized by water in blood could also be used, for example, cross-linked poly 2-hydroxyethyl methacrylate (PHEMA) and its copolymers, e.g., polyacrylamide, and polyvinyl alcohol.

The addition of radiopacifiers (i.e., radiopaque materials) to facilitate tracking and positioning of the stent could be added in any fabrication method or absorbed into or sprayed onto the surface of part or all of the implant. The degree of radiopacity contrast can be altered by implant content. Radiopacity may be imparted by covalently binding iodine to the polymer monomeric building blocks of the elements of the implant. Common radiopaque materials include barium sulfate, bismuth subcarbonate, and zirconium dioxide. Other radiopaque elements include: cadmium, tungsten, gold, tantalum, bismuth, platium, iridium, and rhodium. In one preferred embodiment, iodine may be employed for its radiopacity and antimicrobial properties. Radiopacity is typically determined by fluoroscope or x-ray film.

The stents in accordance with the present invention, may also be useful in vessel grafts, wherein the stent is covered with a sheath formed from either a polymeric material, such as expanded PTFE, degradable polymers, or a natural material, such as fibrin, pericardial tissue, or their derivatives, as will be known to those of skill in the art. The covering may be attached to the inner or outer surface of the stent. Alternatively, the stent may be embedded within layers of the covering material.

Once the stent components have been cut out and assembled into flat modules (see plan views described with respect to FIGS. 1, 2, 4–8, and 11), and linkage elements between adjacent modules have been connected (e.g., by welding, inter-weaving frame elements, etc.), the flat sheets of material are rolled to form a tubular member. Coupling arms from floating coupling elements and end portions are joined (e.g., by welding) to maintain the tubular shape. In embodiments that do not include coupling elements, the end portions of the top and bottom radial elements in a module may be joined. Alternatively, where sliding is desired throughout the entire circumference, a sliding and locking articulation can be made between the end portion of the top radial element and the rib(s) of the bottom radial element (e.g., by tack-welding, heat-staking or snap-together). Similarly, a corresponding articulation can be made between the end portion of the bottom radial element and the rib(s) of the top radial element.

Rolling of the module(s) to form a tubular member can be accomplished by any means known in the art, including rolling between two plates, which are each padded on the side in contact with the stent elements. One plate is held immobile and the other can move laterally with respect to the other. Thus, the stent elements sandwiched between the plates may be rolled about a mandrel by the movement of the plates relative to one another. Alternatively, 3-way spindle methods known in the art may also be used to roll the tubular member. Other rolling methods that may be used in accordance with the present invention include those used for "jelly-roll" designs, as disclosed for example, in U.S. Pat. Nos. 5,421,955, 5,441,515, 5,618,299, 5,443,500, 5,649, 977, 5,643,314 and 5,735,872; the disclosures of which are incorporated herein in their entireties by reference thereto.

The construction of the stent in this fashion provides a great deal of benefit over the prior art. The construction of the locking mechanism is largely material-independent. This allows the structure of the stent to comprise high strength materials, not possible with designs that require deformation of the material to complete the locking mechanism. The incorporation of these materials will allow the thickness required of the material to decrease, while retaining the strength characteristics of thicker stents. In preferred embodiments, the frequency of locking holes or stops present on selected circumferential ribs prevents unnecessary recoil of the stent subsequent to expansion.

Drugs Incorporated into Stents

Drugs and other bioactive compounds can be incorporated into the degradable matrices themselves or coated on the non-degradable stent materials, thereby providing sustained release of such compounds at the site of the stent. In addition, degradable biomaterial can be fabricated in a various forms and processed into the stent components. Preferred biomaterials would incorporate a pharmaceutical agent blended with the degradable polymer prior to fabricating the stent. The preferred pharmaceutical agent(s) control restenosis (including neointimal thickening, intimal hyperplasia and in-stent restenosis or limits vascular smooth muscle cell overgrowth in the lumen of a stented vessel. Other body applications may require different drugs.

In a another aspect of the present invention, the stent biomaterial may also incorporate a hydrogel that acts to prevent adhesions of blood cells, extracellular matrix or other cell types. For instance, NOCC and NOCC—G chitosan. In another aspect, the pharmaceutical agents or hydrogels can be coated onto the surface of the biomaterial singularly or in mixtures or in combination with other binders required to adhere or absorb the pharmaceutical or hydrogel to the biomaterial surface. In addition or in the alternative, the pharmaceutical or hydrogel or genetic material may be incorporated with the biomaterial polymer, microspheres, or hydrogel.

Use of synthetic, natural (plant, microbial, viral or animal-derived) and recombinant forms having selected functions or chemical properties can be mixed with complementary substances (e.g., anti-thrombotic and anti-restenosis substances; nucleic acids and lipid complexes). Pharmacologic agents may also incorporate use of vitamins or minerals. For instance, those that function directly or indirectly through interactions or mechanisms involving amino acids, nucleic acids (DNA, RNA), proteins or peptides (e.g., RGD peptides), carbohydrate moieties, polysaccharides, liposomes, or other cellular components or organelles for instance receptors and ligands.

Pharmaceutical agents may be polar or possess a net negative or positive or neutral charge; they may be hydrophobic, hydrophilic or zwitterionic or have a great affinity for water. Release may occur by controlled release mechanisms, diffusion, interaction with another agent(s) delivered by intravenous injection, aerosolization, or orally. Release may also occur by application of a magnetic field, an electrical field, or use of ultrasound.

The variety of compounds which may be used for coating metallic stents or for incorporating into degradable stent materials have been disclosed by Tanguay et al. *Cardio Clin* (1994) and Nikol et al. *Atherosclerosis* (1996); these references are herein incorporated in their entirety by reference thereto. These compounds include antiplatelet agents (Table 1), antithrombin agents (Table 2), and antiproliferative agents (Table 3). Some preferred agents that fall within these classes of compounds are presented in Tables 1–3 (below).

TABLE 1

| Antiplatelet Agents | |
|---|---|
| Compound | Action |
| Aspirin | Cyclo-oxygenase inhibition |
| Dipyridamole | Phosphodiesterase inhibition |
| Ticlopidine | Blocks interaction between platelet receptors, fibrinogen, and von Willebrand factors |

TABLE 1-continued

| Antiplatelet Agents | |
|---|---|
| Compound | Action |
| C7E3 | Monoclonal antibody to the glycoprotein IIb/IIIa receptor |
| Integrelin | Competitive glycoprotein Iib/IIIa receptor inhibition |
| MK-852, MK-383 | Glycoprotein IIb/IIIa receptor inhibition |
| RO-44-9883 | Glycoprotein IIb/IIIa receptor inhibition |

TABLE 2

| Antithrombin Agents | |
|---|---|
| Compound | Action |
| Heparin | Antithrombin III cofactor |
| Low molecular weight heparin (LMWH) | Inhibition of factor Xa by antithrombin III |
| R-Hirudin | Selective thrombin inhibition |
| Hirulog | Synthetic direct thrombin inhibition |
| Argatroban, efegatran | Synthetic competitive thrombin inhibition |
| Tick anticoagulant peptide | Specific thrombin inhibition |
| Ppack | Irreversible thrombin inhibition |

Additional anti-thrombogenic substances and formulations include endothelium-derived relaxing factor, prostaglandin $I_2$, plasminogen activator inhibitor, tissue-type plasminogen activator (tPA), ReoPro: anti-platelet glycoprotein IIb/IIIa integrin receptor, heparin, polyamine to which dextran sulfate and heparin are covalently bonded, heparin-containing polymer coating for indwelling implants (MEDI-COAT by STS Biopolymers), polyurethaneurea/heparin, hirudin/prostacyclin and analogues, fibrin and fibrin peptide A, lipid-lowering drugs, e.g., Omega-3 fatty acids, and chrysalin (aka TRAP-508) by Chrysalis Vascular Technologies (which is a synthetically manufactured peptide portion of the human enzyme thrombin, responsible for blood clotting and initiating cellular/tissue repair). Chrysalin mimics specific attributes of thrombin by interacting with receptors on cells involved in tissue repair.

Other anti-restenosis substances in accordance with the present invention include INTEGRILIN® (eptifibatide) by COR Therapeutics (blocks platelet clumping), Resten-NG (NeuGene) by AVI BioPharma (synthetic version of C-MYC oncogene), and Implant Sciences Corp., BiodivYsio (phosphorylcholine (PC)) by Abbott Laboratories Inc. and Biocompatibles International PLC, Liposomal Prostaglandin El by Endovasc Ltd. and Collaborative BioAlliance, Adenovirus vectors to carry genes to vascular smooth muscle cells (Boston Scientific Corp and CardioGene Therapeutics Inc.), TAXOL (paclitaxel) by Bristol-Myers Squibb (prevents cell division by promoting the assembly of and inhibiting the disassembly of microtubules), and Rapamycin or nitric oxide. Other drugs include ceramide, tranilast, probucol, statins, cilostazol, and low molecular weight variations of heparin.

A variety of compounds are considered to be useful in controlling vascular restenosis and in-stent restenosis. Some of these preferred antiproliferative agents are presented in Table 3 (below).

TABLE 3

Antiproliferative Agents

| Compound | Action |
| --- | --- |
| Angiopeptin | Somatostatin analog which inhibits IGF-I |
| Ciprostene | Prostacyclin analog |
| Calcium blockers | Inhibition of slow calcium channels |
| Colchicine | Antiproliferative and migration inhibition |
| Cyclosporine | Immunosuppressive, intracellular growth signal inhibition |
| Cytorabine | Antineoplastic, DNA synthesis inhibition |
| Fusion proteins | Toxin-bounded growth factor |
| Lioprost | Prostacyclin analog |
| Ketaserine | Serotonin antagonist |
| Prednisone | Steroid hormone |
| Trapidil | Platelet-derived growth factor inhibitor (inhibitor of thromboxane-A2 and/or PDGF receptor antagonist) |

Specific therapeutic agents have also been identified which may modulate smooth muscle cell (SMC) proliferation. Since SMC cell proliferation has been implicated in atherosclerotic stenosis as well as post-operative restenosis, incorporation of such agents may be particularly useful. These include without limitation, regulators of SMC mitosis (e.g., TAXOL, Rapamycin, or ceramide) and stimulators and triggers for extracellular matrix production, such as anti-FGF and TGF-$\beta_1$ strategies, tissue inhibitor metalloproteinases (TIMPs), and matrix metaloproteinases (MMPs).

Various compounds address specific pathologic events and/or vascular diseases. Some of these therapeutic target compounds are summarized in Table 4 (below).

TABLE 4

Specific Therapeutic Target Compounds

| Pathologic Event | Therapeutic Target |
| --- | --- |
| Endothelial dysfunction | Nitric oxide inducer or antioxidants |
| Endothelial injury | Administer VEGF; FGF's |
| Cell activation & phenotypic modulation | MEF-2 & Gax modulators; NFKB antagonists; cell cycle inhibitors |
| Dysregulated cell growth | E2F decoys; RB mutants; cell cycle inhibitors |
| Dysregulated apoptosis | Bax or CPP32 inducers; Bcl-2 inhibitors; integrin antagonists |
| Thrombosis | IIb/IIIa blockers; tissue factor inhibitors; anti-thrombin agents |
| Plaque rupture | Metalloproteinase inhibitors; leukocyte adhesion blockers |
| Abnormal cell migration | Integrin antagonists: PDGF blockers; plasminogen activator inhibitors |
| Matrix modification | Metalloproteinase inhibitors, plasminogen antagonists; matrix protein cross-linking modifiers |

The therapeutic agents to be bonded to or incorporated within the stent materials of the present invention may be classified in terms of their sites of action in the host. The following agents are believed to exert their actions extracellularly or at specific membrane receptor sites. These include corticoids and other ion channel blockers, growth factors, antibodies, receptor blockers, fusion toxins, extracellular matrix proteins, peptides, or other biomolecules (e.g., hormones, lipids, matrix metalloproteinases, and the like), radiation, anti-inflammatory agents including cytokines such as interleukin-1 (IL-1), and tumor necrosis factor alpha (TNF-$\alpha$), gamma interferon (interferon-$\gamma$), and Tranilast, which modulate the inflammatory response.

Other groups of agents exert their effects at the plasma membrane. These include those involved in the signal transduction cascade, such as coupling proteins, membrane associated and cytoplasmic protein kinases and effectors, tyrosine kinases, growth factor receptors, and adhesion molecules (selectins and integrins).

Some compounds are active within the cytoplasm, including for example, heparin, ribozymes, cytoxins, antisense oligonucleotides, and expression vectors. Other therapeutic approaches are directed at the nucleus. These include gene integration, proto-oncogenes, particularly those important for cell division, nuclear proteins, cell cycle genes, and transcription factors.

Genetic approaches to control restenosis include without limitation: use of antisense oligonucleotides to PDGFR-$\beta\beta$ mRNA to control PDGF expression; use of antisense oligonucleotides for nuclear antigens c-myb or c-myc oncogenes (Bauters et al., 1997, *Trends CV Med*); use of antisense phosphorothioate oligodeoxynucleotides (ODN) against cdk 2 kinase (cyclin dependent kinase) to control the cell cycle of vascular SMC (Morishita et al, 1993, *Hypertension*); use of VEGF gene (or VEGF itself) to stimulate reconstructive wound healing such as endothelialization and decrease neointima growth (Asahara et al 1995); delivery of the nitric oxide synthetase gene (eNOS) to reduce vascular SMC proliferation (Von Der Leyen et al., 1995, *Proc Natl Acad Sci*); use of adenovirus expressing plasminogen activator inhibitor-1 (PAI-1) to reduce vascular SMC migration and thereby diminish restenosis (Carmeliet et al., 1997, *Circulation*); stimulation of apolipoprotein A-1 (ApoAl) over-expression to rebalance serum levels of LDL and HDL; use of apoptosis gene products to promote cell death (of SMC) and cytotactic gene products to that regulate cell division (tumor suppressor protein p53 and Gax homeobox gene product to suppress ras; p21 over expression); and inhibition of NFKB activation (e.g., p65) to control SMC proliferation (Autieri et al., 1994, *Biochem Biophys Res Commun*).

Other therapeutic substances that may be useful as stent coatings and/or depot formulations incorporated within degradable stents include: antibodies to ICAM-1 for inhibition of monocyte chemotactic recruitment and adhesion, macrophage adhesion and associated events (Yasukawa et al, 1996, *Circulation*); toxin based therapies such as chimeric toxins or single toxins to control vascular SMC proliferation (Epstein et al., 1991, *Circulation*); bFGF-saporin to selectively stop SMC proliferation among those cells with a large number of FGF-2 receptors (Chen et al, 1995, *Circulation*), suramin inhibits migration and proliferation by blocking PDGF-induced and/or mitogen activated protein kinase (MAPK-AP-1)-induced signaling (Hu et al., *Circulation*, 1999); Beraprost Sodium, a chemically stable prostacyclin analogue (PG $I_2$), suppresses intimal thickening and lumenal narrowing of coronary arteries. (Kurisu et al., *Hiroshima J. Med Sci,* 1997); Verapamil inhibits neointimal smooth muscle cell proliferation (Brauner et al., *J Thorac Cardiovasc Surg* 1997), agents that block the CD 154 or CD40 receptor may limit the progression of atherosclerosis (E Lutgens et al., *Nature Medicine* 1999), agents that control responses of shear stress response elements or mechanical stress or strain elements or heat shock genes; and anti-chemoattractants for SMC and inflammatory cells.

In addition or in the alternative, cells could be encapsulated in a degradable microsphere, or mixed directly with polymer, or hydrogel and serve as vehicle for pharmaceutical delivery. Living cells could be used to continuously deliver pharmaceutical type molecules, for instance, cytokines and growth factors. Nonliving cells could also serve as a limited or timed release system. Cells or any origin may be used in accordance with this aspect of the present invention. Further, preserved or dehydrated cells which retain their viability when rehydrated may be used. Native, chemically modified (processed), and/or genetically engineered cells may be used.

Stent Deployment

Stents can be deployed in a body lumen by means appropriate to their design. One such method would be to fit the collapsed stent over an inflatable element of a balloon catheter and expand the balloon to force the stent into contact with the body lumen. As the balloon is inflated, the problem material in the vessel is compressed in a direction generally perpendicular to the wall of the vessel which, consequently, dilates the vessel to facilitate blood flow therethrough. Radial expansion of the coronary artery occurs in several different dimensions and is related to the nature of the plaque. Soft, fatty plaque deposits are flattened by the balloon and hardened deposits are cracked and split to enlarge the lumen. It is desirable to have the stent radially expand in a uniform manner.

Alternatively, the stent may be mounted onto a catheter that holds the stent as it is delivered through the body lumen and then releases the stent and allows it to self-expand into contact with the body lumen. This deployment is effected after the stent has been introduced percutaneously, transported transluminally and positioned at a desired location by means of the catheter. The restraining means may comprise a removable sheath.

Figure 14A:
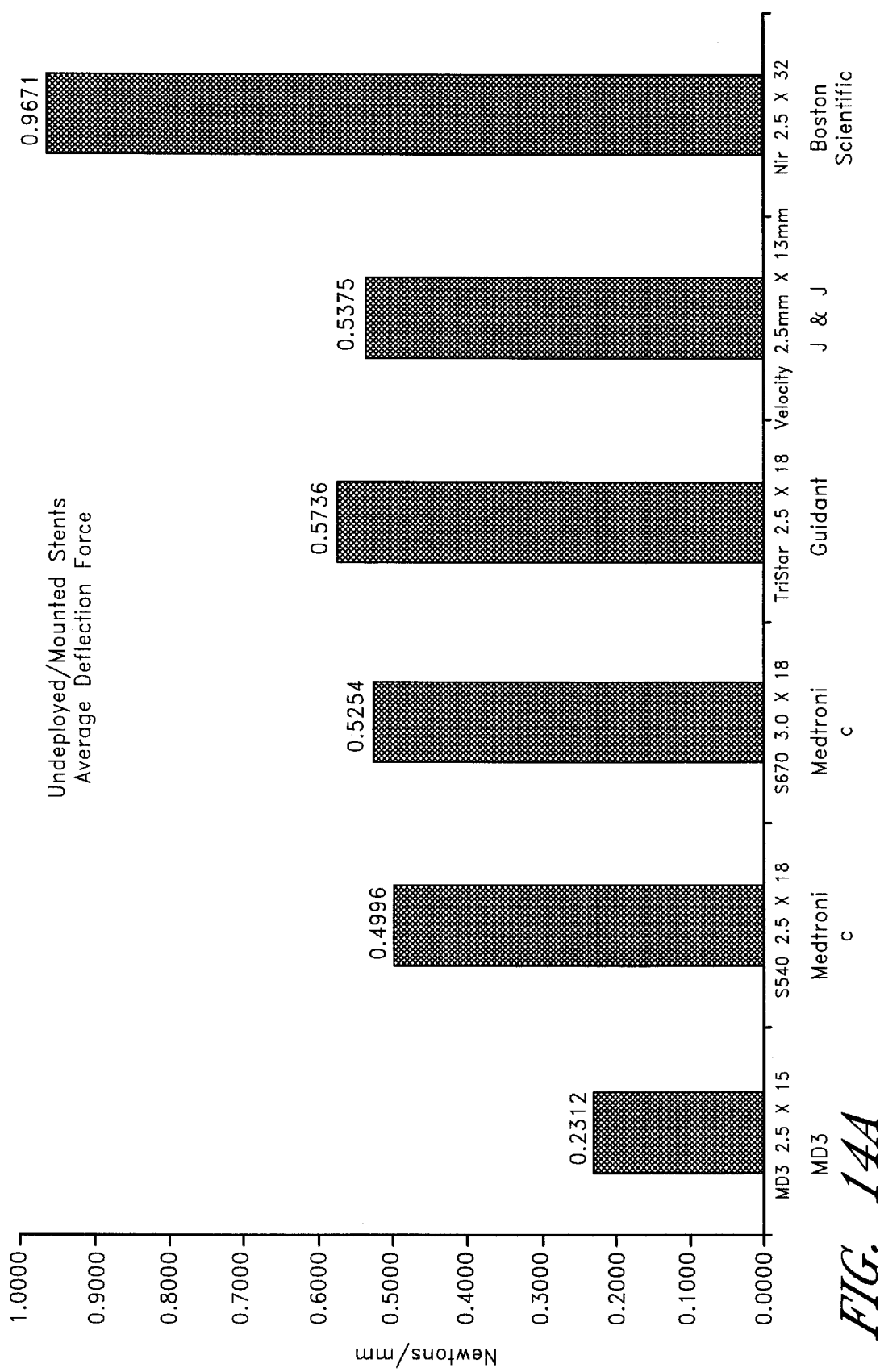
FIGS. 14A and 14B show comparative longitudinal flexibility data for undeployed mounted (collapsed diameter) stents (FIG. 14A) and for deployed (expanded diameter) stents (FIG. 14B).
Figure 14B:
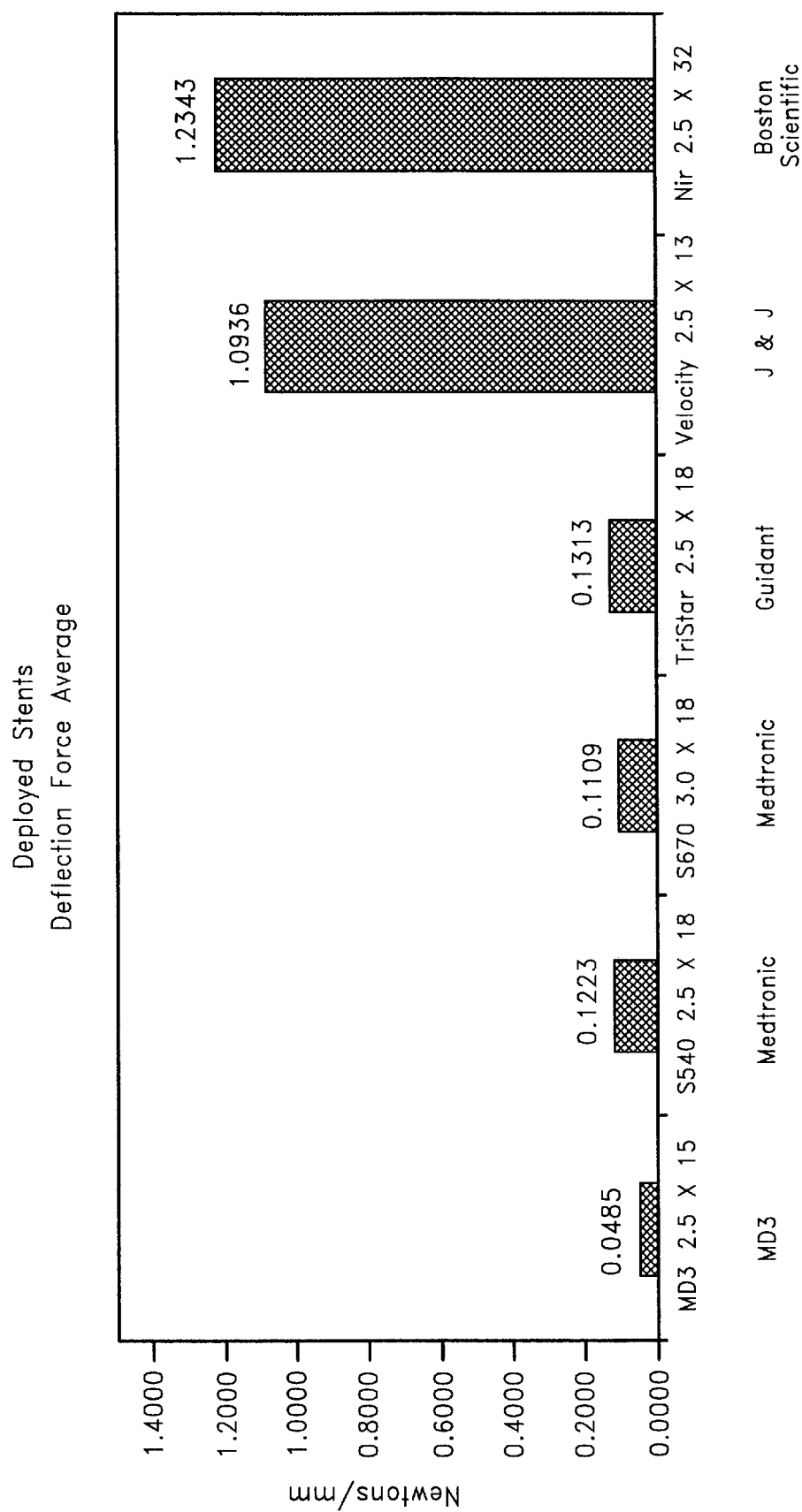

The popular stents in use today are stiffer than desired. Their relative flexibility is shown in FIGS. 14A and 14B. The flexibility of undeployed/mounted stents is shown in FIG. 14A. All deflection tests were conducted in saline at body temperature as defined in the ASTM standards for stent measurements. The S540 (2.5×18 mm) and S670 (3.0×18 mm) stents are produced by Medtronic, the TRISTAR® (2.5×18 mm) is made by Guidant, VELOCITY (2.5×13 mm) is produced by J&J, and the Nir (2.5×32 mm) is marketed by Boston Scientific. The results shown in FIG. 14A (undeployed on a delivery catheter) indicate that the other stents tested are more than 2-fold stiffer than the stent (MD3) made in accordance with the present invention. The difference in flexibility of the deployed (expanded) stents is even more pronounced, as illustrated in FIG. 14B.

Because of the very low profile, small collapsed diameter and great flexibility, stents made in accordance with the present invention may be able to navigate small or torturous paths. Thus, the low-profile stent of the present invention may be useful in coronary arteries, carotid arteries, vascular aneurysms (when covered with a sheath), and peripheral arteries and veins (e.g., renal, iliac, femoral, popliteal, sublavian, aorta, intercranial, etc.). Other nonvascular applications include gastrointestinal, duodenum, biliary ducts, esophagus, urethra, reproductive tracts, trachea, and repiratory (e.g., bronchial) ducts. These applications may or may not require a sheath covering the stent.

The stents of the present invention are adapted for deployment using conventional methods known in the art and employing percutaneous transluminal catheter devices. The stents are designed for deployment by any of a variety of in situ expansion means, such as an inflatable balloon or a polymeric plug that expands upon application of pressure. For example, the tubular body of the stent is first positioned to surround a portion of an inflatable balloon catheter. The stent, with the balloon catheter inside is configured at a first, collapsed diameter. The stent and the inflatable balloon are percutaneously introduced into a body lumen, following a previously positioned guidewire in an over-the-wire angioplasty catheter system, and tracked by a fluoroscope, until the balloon portion and associated stent are positioned within the body passageway at the point where the stent is to be placed. Thereafter, the balloon is inflated and the stent is expanded by the balloon portion from the collapsed diameter to a second expanded diameter. After the stent has been expanded to the desired final expanded diameter, the balloon is deflated and the catheter is withdrawn, leaving the stent in place. The stent may be covered by a removable sheath during delivery to protect both the stent and the vessels.

The expanded diameter is variable and determined by the desired expanded internal diameter of the body passageway. Accordingly, the controlled expansion of the stent is not likely to cause a rupture of the body passageway. Furthermore, the stent will resist recoil because the locking means resist sliding of the elongated ribs within the articulating mechanism on the end portions of the radial elements. Thus, the expanded intraluminal stent will continue to exert radial pressure outward against the wall of the body passageway and will therefore, not migrate away from the desired location.

While a number of preferred embodiments of the invention and variations thereof have been described in detail, other modifications and methods of using and medical applications for the same will be apparent to those of skill in the art. Accordingly, it should be understood that various applications, modifications, and substitutions may be made of equivalents without departing from the spirit of the invention or the scope of the claims.

What is claimed is:

1. An expandable intraluminal stent, comprising:
    a tubular member comprising a clear through-lumen, and having proximal and distal ends and a longitudinal length defined there between, a circumference, and a diameter which is adjustable between at least a first collapsed diameter and at least a second expanded diameter, said tubular member comprising:
        at least one module comprising a series of radial elements, wherein each radial element defines a portion of the circumference of the tubular member and wherein no radial element overlaps with itself in either the first collapsed diameter or the second expanded diameter;
        at least one articulating mechanism which permits one-way sliding of the radial elements from the first collapsed diameter to the second expanded diameter, but inhibits radial recoil from the second expanded diameter; and
        a frame element which surrounds at least one radial element in each module.

2. The expandable intraluminal stent of claim 1, wherein the tubular member comprises at least two modules, and wherein the frame elements from adjacent modules are coupled.

3. The expandable intraluminal stent of claim 2, wherein the frame elements from adjacent modules are coupled by a linkage element extending between the frame elements.

4. The expandable intraluminal stent of claim 2, wherein the frame elements from adjacent modules are coupled by interlinking of the frame elements.

5. The expandable intraluminal stent of claim 1, wherein each radial element comprises at least one elongated rib disposed between first and second portions.

6. The expandable intraluminal stent of claim 5, wherein the radial elements that comprise a module alternate between radial elements having an odd number of elongated ribs and radial elements having an even number of elongated ribs.

7. The expandable intraluminal stent of claim 5, wherein the radial elements that comprise a module alternate between radial elements having one elongated rib and radial elements have two elongated ribs.

8. The expandable intraluminal stent of claim 1, wherein the tubular member comprises at least two modules which are coupled to one another by at least one linkage element.

9. The expandable intraluminal stent of claim 8, wherein the at least one linkage element is made from a degradable material.

10. The expandable intraluminal stent of claim 1, wherein the radial recoil is less than about 5%.

11. The expandable intraluminal stent of claim 1, wherein said tubular member has a stiffness of s than about 0.1 Newtons force/millimeter deflection.

12. The expandable intraluminal stent of claim 1, wherein said tubular member provides a surface area coverage of greater than about 20%.

13. The expandable intraluminal stent of claim 1, wherein the tubular member is at least partially radiopaque.

14. The expandable intraluminal stent of claim 1, wherein said radial elements are made substantially from a material which is work hardened to between about 25% and 95%.

15. The expandable intraluminal stent of claim 1, the expandable intraluminal wherein the radial elements are made from a material selected from the group consisting of a polymer, a metal, a ceramic, and combinations thereof.

16. The expandable intraluminal stent of claim 15, wherein said material further comprise a bioactive agent.

17. The expandable intraluminal stent of claim 16, wherein the radial elements are adapted to release the bioactive agent during stent deployment when the tubular member is adjusted from the first collapsed diameter to the second expanded diameter.

18. The expandable intraluminal stent of claim 16, wherein the bioactive agent is selected from the group consisting of antiplatelet agents, antithrombin agents, antiproliferative agents and antiinflammatory agents.

19. The expandable intraluminal stent of claim 1, wherein the radial elements are made from a degradable material.

20. The expandable intraluminal stent of claim 19, wherein said degradable material is selected from the group consisting of polyarylates (L-tyrosine-derived), free acid polyarylates, polycarbonates (L-tyrosine-derived), poly(ester-amides), poly(propylene fumarate-co-ethylene glycol) copolymer, polyanhydride esters, polyanhydrides, polyorthoesters, silk-elastin polymers, calcium phosphate and magnesium alloys.

21. The expandable intraluminal stent of claim 19, wherein said degradable material further co rises a bioactive agent, which is released as the material degrades.

22. The expandable intraluminal stent of claim 21, wherein said degradable material is adapted to deliver an amount of the bioactive agent which is sufficient to inhibit restenosis at a site of stent deployment.

23. The expandable intraluminal stent of claim 21, wherein the bioactive agent is selected from the group consisting of antiplatelet agents, antithrombin agents, antiproliferative agents and inflammatory agents.

24. The expandable intraluminal stent of claim 1, comprising at least two modules, wherein the expanded diameters of the first and second modules are different.

25. The expandable intraluminal stent of claim 1, wherein each articulating mechanism comprises a slot and a tab on one radial element and at least one stop on an adjacent radial element which is slideably engaged in the slot, wherein the tab is adapted to engage the at least one stop.

26. The expandable intraluminal stent of claim 25, wherein the at least one stop comprises a hole with a chamfered edge.

27. The expandable intraluminal stent of claim 25, wherein the least one articulating mechanism further comprises an expansion resistor on the slideably engaged radial element, wherein the expansion resistor resists passing through the slot during expansion until further force is applied, such that the radial elements in the module expand in a substantially uniform manner.

28. The expandable intraluminal stent of claim 1, wherein the articulating mechanism further comprises a release, such that actuation of the release permits sliding of the radial elements of the second expanded diameter back to the first collapse diameter.

29. The expandable intraluminal stent of claim 1, further comprising a floating coupling element with an articulating mechanism.

* * * * *

UNITED STATES PATENT AND TRADEMARK OFFICE
CERTIFICATE OF CORRECTION

PATENT NO. : 6,623,521 B2
DATED : September 23, 2003
INVENTOR(S) : Thomas A. Steinke, Donald H. Koenig and Joan Zeltinger It is certified that error appears in the above-identified patent and that said Letters Patent is hereby corrected as shown below:

Column 24,
Line 65, please delete "second portions" and insert therefore, -- second end portions --.

Column 25,
Line 7, please delete "have" and insert therefore, --having -- .
Line 17, please delete "of s than" and insert therefore, -- of less than --.
Line 32, please delete "comprise" and insert therefore, -- comprises --.

Column 26,
Line 8, please delete "co rises" and insert therefore, -- comprises --.
Line 17, please delete "inflammatory agents" and insert therefore, -- anti-inflammatory agents --.
Line 40, please delete "collapse" and insert therefore, -- collapsed --.

Signed and Sealed this

Sixth Day of July, 2004

JON W. DUDAS
*Acting Director of the United States Patent and Trademark Office*